(12) United States Patent
Owen et al.

(10) Patent No.: US 7,621,873 B2
(45) Date of Patent: Nov. 24, 2009

(54) METHOD AND SYSTEM TO SYNCHRONIZE ACOUSTIC THERAPY WITH ULTRASOUND IMAGING

(75) Inventors: Neil Owen, Seattle, WA (US); Michael R. Bailey, Seattle, WA (US); James Hossack, Duvall, WA (US)

(73) Assignee: University of Washington, Seattle, WA (US)

( * ) Notice: Subject to any disclaimer, the term of this patent is extended or adjusted under 35 U.S.C. 154(b) by 531 days.

(21) Appl. No.: 11/206,640

(22) Filed: Aug. 17, 2005

(65) Prior Publication Data

US 2007/0055155 A1 Mar. 8, 2007

(51) Int. Cl.
*A61B 17/22* (2006.01)
(52) U.S. Cl. .............................. 600/459; 601/3; 601/2; 601/4; 310/311; 310/322; 310/334; 600/439
(58) Field of Classification Search ................ 600/439, 600/443, 437, 459; 601/2, 3, 4; 607/72; 29/59; 310/311, 322, 334
See application file for complete search history.

(56) References Cited

U.S. PATENT DOCUMENTS

| 125,623 | A | * | 4/1872 | Kelly et al. ................. 70/170 |
| RE33,590 | E | | 5/1991 | Dory ...................... 128/660.03 |
| 5,039,774 | A | | 8/1991 | Shikinami et al. ............. 528/60 |
| 5,065,742 | A | | 11/1991 | Belikan et al. ................ 128/24 |
| 5,080,101 | A | | 1/1992 | Dory ...................... 128/660.03 |
| 5,080,102 | A | | 1/1992 | Dory ...................... 128/660.03 |
| 5,150,712 | A | | 9/1992 | Dory ...................... 128/660.03 |
| 5,219,401 | A | | 6/1993 | Cathignol et al. ......... 128/660.03 |
| 5,311,869 | A | | 5/1994 | Okazaki ................. 128/660.03 |
| 5,391,140 | A | | 2/1995 | Schaetzle et al. .............. 601/4 |
| 5,394,877 | A | | 3/1995 | Orr et al. ..................... 600/459 |

(Continued)

FOREIGN PATENT DOCUMENTS

DE 04230415 A1 3/1994

(Continued)

OTHER PUBLICATIONS

Vaezy, Shahram et al. 2001. "Acoustic surgery." *Physics World* (August): 35-39.

(Continued)

*Primary Examiner*—Long V Le
*Assistant Examiner*—Joel F Brutus
(74) *Attorney, Agent, or Firm*—Ronald M. Anderson

(57) ABSTRACT

Interference in ultrasound imaging when used in connection with high intensity focused ultrasound (HIFU) is avoided by employing a synchronization signal to control the HIFU signal. Unless the timing of the HIFU transducer is controlled, its output will substantially overwhelm the signal produced by ultrasound imaging system and obscure the image it produces. The synchronization signal employed to control the HIFU transducer is obtained without requiring modification of the ultrasound imaging system. Signals corresponding to scattered ultrasound imaging waves are collected using either the HIFU transducer or a dedicated receiver. A synchronization processor manipulates the scattered ultrasound imaging signals to achieve the synchronization signal, which is then used to control the HIFU bursts so as to substantially reduce or eliminate HIFU interference in the ultrasound image. The synchronization processor can alternatively be implemented using a computing device or an application-specific circuit.

32 Claims, 16 Drawing Sheets

U.S. PATENT DOCUMENTS

| | | | | |
|---|---|---|---|---|
| 5,471,988 | A | 12/1995 | Fujio et al. | 128/660.03 |
| 5,474,071 | A | 12/1995 | Chapelon et al. | 600/439 |
| 5,492,126 | A | 2/1996 | Hennige et al. | 600/439 |
| 5,507,790 | A | 4/1996 | Weiss | 607/100 |
| 5,522,878 | A | 6/1996 | Montecalvo et al. | 607/152 |
| 5,526,815 | A | 6/1996 | Granz et al. | 128/660.03 |
| 5,558,092 | A | 9/1996 | Unger et al. | 128/660.03 |
| 5,573,497 | A | 11/1996 | Chapelon | 601/2 |
| 5,666,954 | A | 9/1997 | Chapelon et al. | 600/439 |
| 5,720,286 | A | 2/1998 | Chapelon et al. | 600/439 |
| 5,720,287 | A | 2/1998 | Chapelon et al. | 600/439 |
| 5,769,790 | A | 6/1998 | Watkins et al. | 600/439 |
| 5,817,021 | A | 10/1998 | Reichenberger | 600/439 |
| 5,823,962 | A | 10/1998 | Schaetzle et al. | 600/439 |
| 5,827,204 | A | 10/1998 | Grandia et al. | 601/2 |
| 5,833,647 | A | 11/1998 | Edwards | 604/22 |
| 5,873,828 | A | 2/1999 | Fujio et al. | 600/439 |
| 5,895,356 | A | 4/1999 | Andrus et al. | 600/439 |
| 5,993,389 | A | 11/1999 | Driscoll, Jr. et al. | 600/371 |
| 6,007,499 | A | 12/1999 | Martin et al. | 601/3 |
| 6,039,694 | A | 3/2000 | Larson et al. | 600/459 |
| 6,050,943 | A | 4/2000 | Slayton et al. | 600/439 |
| 6,179,831 | B1 | 1/2001 | Bliweis | 606/21 |
| 6,221,015 | B1 | 4/2001 | Yock | 600/439 |
| 6,409,720 | B1 | 6/2002 | Hissong et al. | 606/27 |
| 6,425,867 | B1 | 7/2002 | Vaezy | 600/439 |
| 6,491,672 | B2 | 12/2002 | Slepian et al. | 604/267 |
| 6,595,934 | B1 | 7/2003 | Hissong et al. | 601/3 |
| 6,599,256 | B1 | 7/2003 | Acker et al. | 601/2 |
| 6,626,855 | B1 * | 9/2003 | Weng et al. | 601/3 |
| 6,633,658 | B1 | 10/2003 | Dabney et al. | 382/128 |
| 6,656,136 | B1 | 12/2003 | Weng et al. | 601/2 |
| 6,676,601 | B1 * | 1/2004 | Lacoste et al. | 600/439 |
| 6,685,639 | B1 | 2/2004 | Wang et al. | 600/439 |
| 6,716,184 | B2 * | 4/2004 | Vaezy et al. | 601/3 |
| 6,719,699 | B2 | 4/2004 | Smith | 600/459 |
| 6,726,627 | B1 * | 4/2004 | Lizzi et al. | 600/439 |
| 6,846,291 | B2 | 1/2005 | Smith et al. | 600/459 |
| 2002/0193681 | A1 | 12/2002 | Vitek et al. | 600/411 |
| 2003/0069569 | A1 | 4/2003 | Burdette et al. | 606/27 |
| 2003/0125623 | A1 | 7/2003 | Kelly et al. | 600/437 |
| 2004/0019278 | A1 | 1/2004 | Abend | 600/545 |
| 2004/0030268 | A1 * | 2/2004 | Weng et al. | 601/2 |
| 2004/0078034 | A1 | 4/2004 | Acker et al. | 606/27 |
| 2004/0097805 | A1 | 5/2004 | Verard et al. | 600/428 |
| 2004/0097840 | A1 | 5/2004 | Holmer | 601/2 |
| 2004/0122493 | A1 * | 6/2004 | Ishibashi et al. | 607/96 |
| 2004/0143186 | A1 | 7/2004 | Anisimov et al. | 600/437 |
| 2004/0153126 | A1 | 8/2004 | Okai | 607/1 |
| 2004/0181178 | A1 | 9/2004 | Aldrich et al. | 601/3 |
| 2004/0234453 | A1 | 11/2004 | Smith | 424/9.5 |

FOREIGN PATENT DOCUMENTS

| | | |
|---|---|---|
| EP | 01265223 B1 | 11/2002 |
| WO | WO 00/72919 | 12/2000 |

OTHER PUBLICATIONS

Vaezy, Shahram et al. 2001. "Experimental Investigations and Device Development." First International Workshop on the Application of HIFU in Medicine. (May 1-13): 4pp.

Ostensen, Jonny, PhD; Bendiksen, Ragner, MSc. "Characterization and Use of Ultrasound Contrast Agents." *Acad Radiol* 2002; 9(suppl 2):S276-S278.

Klibanov, Alexander L.; Rasche, Peter T.; Hughes, Michael S.; Wojdyla, Jolette K.; Galen, Karen P.; Wiblee, James H.; Brandenburger, Gary H. "Detection of Individual Microbubbles of an Ultrasound contrast Agent: Fundamental and Pulse Inversion Imaging[1]." *Acad Radiol* 2002, 9(suppl 2):S279-S281.

Bauer, A.; Solbiati, L.; Weissman, N. "Ultrasound Imaging with SonoVue: Low Mechanical Index Real-time Imaging." *Acad Radiol* 2002, 9(suppl 2):S282-S284.

Watkin, Kenneth L., PhD; McDonald, Michael A., BS. "Multi-Modal Contrast Agents: A First Step[1]." *Acad Radiol* 2002, 9(suppl 2):S285-S287.

Watkin, Kenneth L., PhD; McDonald, Michael A., BS. "Schematic of the Tube, Cross Section Ultrasound Images of the Tube With Different Contrast Media (CM)." *Acad Radiol* 2002,9(suppl 2):S288-S289.

Wickline, Samuel A., MD; Hughes, Michael, PhD; Ngo, Francis C., MD; Hall, Christopher, S., PhD; Marsh, Jon, N., PhD; Brown, Peggy A; Allen, John S., BS; McLean, Mark D.; Scott, Michael J., BS; Fuhrhop, Ralph W.; Lanza, Gregory M., MD, PhD. "Blood Contrast Enhancement with a Novel, Non-Gaseous Nanoparticle Contrast Agent[1]," *Acad Radiol* 2002, 9(suppl 2):S290-S293.

Indman, Paul, MD, "Alternatives in Gynecology." Hysteroscopy © 2000 OBGYN.net <http://www.gynalternatives.com/hsc.html>.

Kaczkowski, Peter J.; Vaezy, Shahram; Martin, Roy; Crum, Lawrence. "Development of a High Intensity Focused Ultrasound System for Image-Guided Ultrasonic Surgery." Ultrasound for Surgery 2001. <http://cimu.apl.washington.edu/hifusurgerysystem.html>.

Physicians. "Breast Cancer—Insightec: focused ultrasound for non invasive treatment." FAQ <http://www.exablate2000.com/physicians_faq.html>.

Owaki, T., Nakano, S. Arimura, K., Aikou, T. "The Ultrasonic Coagulating and Cutting System Injuries Nerve Function." *First Department of Surgery, Kagoshima University School of Medicine, Kagoshima, Japan, Endoscopy*. (2002): 575-579.

Rivens, I.H., Rowland, I.J., Denbow, M., Fisk, N.M., Harr, G.R., Leach, M.O. "Vascular Occlusion Using Focused Ultrasound Surgery for Use in Fetal Medicine." *European Journal of Ultrasound 9* (1999): pp. 89-97.

Tachibana, Katsuro and Shunro MD, PhD. "The Use of Ultrasound for Drug Delivery." *First Department of Anatomy, Fukuoka University School of Medicine*, Nanakuma, Japan,Echocardiography. (2001): 323-328.

Ka-yun Ng, Yang Liu. "Therapeutic Ultrasound: Its Application in Drug Delivery." Medicinal Research Reviews, vol. 22, 204-223, 2002.

Porter, T.R., Xie, F. "Ultrasound, Microbubbles and Thrombolysis." Progress in Cardiovascular Diseases, vol. 44, No. 2, Oct. 2001: 101-110.

Nobuki Kudo, Takehiro Miyaoka, Kengo Okada, and Katsuyuki Yamamoto. "Study on Mechanism of Cell Damage Cased by Microbubbles Exposed to Ultrasound." *Graduate School of Engineering, Hokkaido University, Japan, Research Institute for Electronic Science, Hokkaido University*, 060-0812 Japan.

Holt, Glynn R., Roy, Ronald A., Edson, Patrick A., Yang, Xinmai. "Bubbles and Hifu: the Good, the Bad and the Ugly." *Boston University, Department of Aerospace and Mechanical Engineering*, Boston, MA 02215: 120-131.

Everbach, Carr E. and Charles W. Francis. "Cavitational Mechanisms in Ultrasound-Accelerated Thrombolysis at 1 MHz." Ultrasound in Med. & Biol., vol. 26, No. 7, pp. 1153-1160, 2000.

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305-1320, 1999. Copyright 1999 World Federation for Ultrasound in Medicine & Biology.

Poliachik, Sandra L., et al. "Effect of High-Intensity Focused Ultrasound on Whole Blood With or Without Microbubble Contrast Agent." Ultrasound in Med. & Biol., vol. 25, No. 6, 1999: 991-998.

Poliachik, Sandra L., et al. "Activation, Aggregation and Adhesion of Platelets Exposed to High-Intensity Focused Ultrasound." Ultrasound in Med. & Biol., vol. 27, No. 11, pp. 1567-1576, 2001.

Rosenschein, Uri, et al. "Ultrasound Imaging-Guided Nonivasive Ultrasound Thrombolysis-Preclinical Results." © 2000 American Heart Association, Inc. (Circulation. 2000;102:238-245.) <http://www.circulationaha.com.org>.

Tachibana, Katsuro, and Shunro MD, PhD. "Albumin Microbubble Echo-Contrast Material as an Enhancer for Ultrasound Accelerated Thrombolysis." (Circulation, 1995;92: 1148-1150.) © 1995 American Heart Association, Inc.

Miller, Morton W. et al. "A Review of In Vitro Bioeffects of Inertial Ultrasonic Cavitation From a Mechanistic Perspective." Ultrasound in Med. & Biol., vol. 22, No. 9, pp. 1131-1154, 1996.

Rosenschein, Uri, et al. "Shock-Wave Thrombus Ablation, A New Method for Noninvasive Mechanical Thrombolysis." The American Journal of Cardiology, vol. 70, Issue 15, Nov. 1992: pp. 1358-1361.

Guzman, Hector R. et al. "Ultrasound-mediated disruption of cell membranes. II. Heterogeneous effects on cells." J. Acoust. Soc. Am 110 (1), Jul. 2001: pp. 597-606.

Guzman, Hector R. et al. "Ultrasound-Mediated Disruption of Cell Membranes. I. Quantification of Molecular uptake and Cell Viability." J. Acoust. Soc. Am. 110 (1), Jul. 2001: pp. 588-595.

Hynynen, Kullervo et al. "Potential Adverse Effects of High-Intensity Focused Ultrasound Exposure on Blood Vessels In Vivo." Ultrasound in Med. & Biol., vol. 22, No. 2, pp. 193-201, 1996.

Chen, Wen-Shiang et al. "A comparison of the fragmentation thresholds and inertial cavitation doses of different ultrasound contrast agents." J. Acoust. Soc. Am. 113 (1), Jan. 2003: pp. 643-651.

Dayton, Paul A. et al. "The magnitude of radiation force on ultrasound contrast agents." J. Acoust. Soc. Am. 112 (5) Pt. 1, Nov. 2002: pp. 2183-2192.

"Mechanical Bioeffects in the Prescence of Gas-Carrier Ultrasound Contrast Agents." J Ultrasound Med. 19: 120-142, 2000.

Chen, Wen-Shiang, et al. "Inertial Cavitation Dose and Hemolysis Produced In Vitro with or Without Optison." Ultrasound in Med. & Biol., vol. 29, No. 5, pp. 725-737, 2003.

Anand, Ajay et al. "Using the ATL 1000 to Collect Domodulated RF Data for Monitoring HIFU Lesion Formation." Center for Industrial and Medical Ultrasound, University of Washington. Abstract. 11pp.

Bauer, A.; Solbiati, L.; Weissman, N. "Ultrasound Imaging with Sono Vue: Low Mechanical Index Real-time Imaging." Acad Radiol 2002, 9(suppl 2):S282-S284.

Hatangadi, Ram Bansidhar. "A Novel Dual Axis Multiplanar Transesophageal Ultrasound Probe for Three-Dimensional Echocardiograph." *University of Washington, Department of Sciences and Engineering*. (1994), Abstract. vol. 55-11B: 1pg.

Indman, Paul, MD,. "Alternatives in Gynecology." Hysteroscopy © 2000 OBGYN.net <http://www.gynalternatives.com/hsc.html>.

Kaczkowski, Peter J., Vaezy, Shahram, Martin, Roy, Crum, Lawrence. "Development of a High Intensity Focused Ultrasound System for image-guided ultrasonic surgery." Ultrasound for Surgery 2001. <http://cimu.apl.washington.edu/hifusurgerysystem.html>.

Klibanov, Alexander L; Rasche, Peter T.; Hughes, Michael S.; Wojdyla, Jolette K.; Galen, Karen P.; Wiblee, James H.; Brandenburger, Gary H.. "Detection of Individual Microbubbles of an Ultrasound contrast Agent: Fundamental and Pulse Inversion Imaging[1]." *Acad Radiol* 2002, 9(suppl 2):S279-S281.

Owaki, T., Nakano, S. Arimura, K., Aikou, T. "The Ultrasonic Coagulating and Cutting System Injuries Nerve Function." *First Department of Surgery, Kagoshima University School of Medicine, Kagoshima, Japan, Endoscopy*. (2002) 575-579.

* cited by examiner

METHOD AND SYSTEM TO SYNCHRONIZE ACOUSTIC THERAPY WITH ULTRASOUND IMAGING

GOVERNMENT RIGHTS

This invention was made with U.S. Government support under grant No. SMS00203 awarded by NASA and the National Space Biomedical Research Institute. The U.S. Government has certain rights in the invention.

FIELD OF THE INVENTION

The present invention relates to apparatus and methods for simultaneously using ultrasound imaging waves and ultrasound therapy waves, and more specifically, to apparatus and method designed to enable real-time, noise-free ultrasound imaging of a target area proximate a focal region associated with the ultrasound therapy waves.

BACKGROUND OF THE INVENTION

Acoustic therapies include shock wave lithotripsy (SWL), high intensity focused ultrasound (HIFU), and ultrasound-enhanced drug delivery. HIFU is used for many therapeutic applications, including hemostasis, tumor treatment, and tissue necrosis. These procedures are made possible by the unique ability of such acoustic therapy technologies to selectively apply relatively large amounts of therapeutic energy (on the order of 1000 W/cm$^2$) to a treatment volume disposed deep within a body mass, without adversely affecting tissue disposed between an acoustic therapy transducer that produces the energy and the treatment volume. HIFU, in particular, is a powerful medical technique with great potential and is currently being employed, both in the United States and abroad, to treat tumors. However, to safely implement non-invasive, HIFU-based transcutaneous acoustic surgery, a medical imaging modality must be used to visualize the internal treatment site, for targeting the site and monitoring the treatment process. Ultrasound imaging is an attractive modality for the following reasons: (a) images are available in real-time; (b) portable imagers are commercially available; (c) Doppler-based imaging modalities can be used to detect bleeding; (d) ultrasound imaging is a relatively ubiquitous medical technology; and, (e) ultrasound imaging is relatively inexpensive, compared to other medical imaging systems, such as magnetic resonance imaging (MRI).

A problem with combining HIFU therapy with ultrasound imaging is that the high energy therapeutic waves introduces a significant amount of noise into an ultrasound imaging signal employed to monitor the treatment site, making simultaneous imaging and treatment difficult. Indeed, the high energy of the HIFU wave can completely overwhelm conventional ultrasonic imaging systems. One analogy that might help to make this problem clear relates to relative intensities of light. Consider the light coming from a star in the evening sky to be analogous to the low power imaging ultrasound waves that are reflected from a target area toward the imaging transducer, while the light from the sun is analogous to the HIFU waves generated by the therapy transducer. When the sun is out, the light from the stars is completely overwhelmed by the light from the sun, and a person looking into the sky is unable to see any stars, because the bright light from the sun completely masks the dim light coming from the stars. Similarly, the HIFU waves emitted by the therapy transducer completely overwhelm the lower energy imaging ultrasound waves produced by the imaging transducer, and any ultrasonic image generated is saturated with noise caused by the HIFU wave from the therapeutic transducer.

FIG. 1A schematically illustrates a prior art ultrasound image 10 in which a scanned field 12 is completely obscured by noise 14, caused by the simultaneous operation of an ultrasound imaging pulse (i.e., an ultrasound imaging wave) and a HIFU wave (neither shown). In ultrasound image 10, a clinician may be attempting to focus the HIFU wave on a treatment site 18. However, because noise 14 completely saturates scanned field 12, it is impossible to accurately focus the HIFU wave onto treatment site 18. If the therapy transducer is completely de-energized, noise 14 is eliminated from the scanned field. However, under these conditions, the focal point of the HIFU wave will not be seen, and thus, the HIFU wave cannot be accurately focused on treatment site 18. While some change in echogenicity at the HIFU focal point may persist for a time even after the HIFU wave is no longer active, any change in a position of the therapy transducer (or treatment site 18) will not register until the therapeutic transducer is re-energized. Thus, the HIFU wave cannot be focused in real time.

Some prior art systems have included a targeting icon in an ultrasound image to indicate where the known focal point of a specific HIFU transducer would be located in a scanned image. While this icon may be helpful in determining a position of the focal region of the HIFU transducer relative to the scanned ultrasound image, such an icon based technique does not enable a clinician to observe real-time results. Once the HIFU therapeutic transducer is energized, the scanned ultrasound image is completely saturated with noise, and the clinician cannot monitor the progress of the treatment without again de-energizing the HIFU therapeutic transducer. Furthermore, it should be noted that the accuracy of such icon-based targeting systems generally degrades during treatment due to changes in refraction, temperature of the tissue, the presence bubbles in or near the target area, and patient movement (including movement associated with respiration).

FIG. 1B schematically illustrates a prior art technique disclosed in U.S. Pat. No. 6,425,867 (the disclosure, specification and drawings of which are hereby specifically incorporated by reference) for reducing the amount of noise disrupting an ultrasound image during HIFU therapy. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging pulses generated by the scanning transducer. In FIG. 1B, noise 24 substantially masks a treatment site 28. This result would not occur in all cases, because to an observer, noise 24 would move across scanned field 22 as the interference between the HIFU waves and the imaging pulses varies in time. Pulsing of the HIFU wave alone would thus enable the clinician to view a noise-free image of the treatment site only when noise 24 was randomly shifted to a different part of scanned field 22, away from the treatment site. However, such pulsing alone generates an image that is extremely distracting to a clinician, because noise 24 flickers across scanned field 22, making it difficult to concentrate and difficult to consistently determine where the focal point of the HIFU wave is, relative to the treatment site, in real time.

FIG. 1C schematically illustrates another prior art technique that is disclosed in U.S. Pat. No. 6,425,867 (referred to hereafter as the '867 patent), also for reducing the amount of noise disrupting an ultrasound image during HIFU therapy. In an ultrasound image 30, a HIFU wave from a therapy transducer has been both pulsed and synchronized with respect to the ultrasonic imaging pulses from an imaging transducer, to ensure that noise 34 does not obscure a treatment site 38. In ultrasound image 30, noise 34 has been shifted to a location within a scanned field 32 that is spaced apart from treatment site 38, by selectively adjusting both the pulsing and the synchronization of the HIFU wave. Preferably, noise 34 is shifted completely away from treatment site 38, thus providing the clinician a noise-free, stable image of treatment site 38 that clearly shows the location of the focal point of the HIFU wave relative to the treatment site. Thus, the HIFU wave can be focused onto treatment site 38, in real time. By synchronizing the HIFU bursts within each imaging frame, the interference can be relegated to certain portions of the image, such as a fringe of the ultrasound image, enabling other portions of the ultrasound image to remain useful for monitoring and guidance. If the imaging process and the HIFU bursts are not synchronized, the interference will randomly obscure the treatment site, as indicated in FIG. 1B.

FIG. 2 is a block diagram from the '867 patent, schematically illustrating a system that synchronizes the ultrasound image and HIFU waves required for the simultaneous imaging and therapy in real time. A conventional imaging probe 44 is connected to an ultrasound imaging machine 40 via a cable 42. Imaging probe 44 generates ultrasonic imaging pulses that propagate to the target area, are reflected from structure and tissue within the body, and are received by the imaging probe. The signal produced by the imaging probe in response to the reflected ultrasound imaging waves is communicated to the ultrasound imaging machine through cable 42 and processed to provide a visual representation of the structure and tissue that reflected the ultrasonic imaging pulses. An imaging beam sector 46 (indicated by dotted lines) from imaging probe 44 is identified in the Figure by dash lines. The system described in the '867 patent also includes a therapeutic transducer 60. When excited, this therapeutic transducer generates HIFU waves that are focused at a particular point of interest, i.e., a treatment site within a patient's body. In FIG. 2, the path of a HIFU beam 62 (indicated by solid lines) narrows to a focal point 64.

Synchronization output signal 48 is supplied to a synchronization delay 50, which enables the user to selectively vary the initiation of each HIFU wave with respect to each sequence of ultrasonic imaging pulses that are generated to form an ultrasonic image. Referring to FIG. 1C, delay 50 enables a user to vary the position of noise 34 in scanned field 32, so that the noise is moved away from treatment site 38, to a different portion of scanned field 32. A HIFU duration circuit 52 is used to control the duration of the HIFU wave. A longer duration HIFU wave will apply more energy to the treatment site. If the HIFU wave is too long, the duration of noise 34 as shown in ultrasound image 30 will increase and can extend into the next ultrasound imaging pulse to obscure treatment site 28, or may completely obscure ultrasound image 30, generating a display very similar to ultrasound image 10 in FIG. 1A. Thus, the user will have to selectively (i.e., manually) adjust HIFU duration circuit 52 to obtain a noise-free image of treatment site 38, while providing a sufficient level of energy to the treatment site to affect the desired therapeutic effect in an acceptable time. A HIFU excitation frequency generator 56 is used to generate the desired frequency for the HIFU wave, and a power amplifier 58 is used to amplify the signal produced by the HIFU excitation frequency generator to achieve the desired energy level of the HIFU wave. Power amplifier 58 is thus adjustable to obtain a desired energy level for the HIFU wave.

Significantly, the system disclosed in the '867 patent requires modifying a conventional ultrasound imaging machine to achieve modified ultrasound imaging machine 40, which is capable of providing synchronization output signal 48. The '867 patent notes that such a synchronization output signal is not normally provided in prior art ultrasound imaging machines. The '867 patent suggests that if an ultrasound imaging machine capable of providing the synchronization output signal is not available, then a synchronization output signal can be derived from the ultrasound imaging signals conveyed by cable 42. The '867 patent also suggests that an optional stable synchronization signal generator 66 can be used to synchronize the HIFU wave to the imaging ultrasonic wave, instead of using synchronization output signal 48 from ultrasound imaging machine 40. Stable synchronization signal generator 66 can be used to provide a stable synchronizing pulse to initiate the HIFU wave, and the timing of this stable synchronizing pulse can be manually varied until a noise-free image of the treatment site has been obtained. A drawback of using stable synchronization signal generator 66 instead of synchronization output signal 48 is that any change in the timing of the ultrasound imaging pulses, such as is required to scan deeper within tissue, will require to the user to again adjust stable synchronization signal generator 66. Such an adjustment would not be required if synchronization output signal 48 were used. It should be noted that one drawback of using synchronization output signal 48 is that the ultrasound imaging system must be modified or custom built to provide such a synchronization signal. Furthermore, some imaging modalities, such as Doppler imaging, have very complex signals, and synchronization output signal 48 may not be very effective for synchronizing such complex signals.

Essentially, the '867 patent addresses HIFU interference of ultrasound imaging by synchronizing the interference so that the interference is stable and is located at the fringes of the image. As a result, the region of interest in the image is not obscured (as is schematically indicated in FIG. 1C). This functionality requires knowledge of the frame rate and phase of the imaging cycle, both of which vary with changes to user control settings (particularly depth and switching modality from b-mode to Doppler). Once the frame rate and phase are known, HIFU can be gated synchronously with the imaging cycle and the interference that is caused can be moved to the fringes of the image. Unfortunately, there is no simple way of determining the frame rate and phase of a stand-alone commercial imager that has not been designed to provide such information (i.e., which has not been modified to provide synchronization output signal 48).

As indicated in the '867 patent, ultrasound imaging systems can be designed to incorporate a synchronization output signal. However, even though ultrasound imaging systems are significantly less expensive than MRI imaging systems, high end ultrasound imaging systems can still cost in excess of $150,000, and it would be desirable to provide a synchronization technique that is compatible with ultrasound imaging systems that do not provide a synchronization output signal (the majority of ultrasound imaging systems sold do not support the synchronization output signal as described in the '867 patent). The '867 patent also suggests that the synchronization signal (frame rate without phase information) could be obtained from the cable coupling an ultrasound imaging probe to ultrasound imaging machines. This theoretically could be achieved by detecting current in the cable. However, such cables include many wires and currents, and such cables are well shielded to meet safety standards. Hence, obtaining the signal necessary for synchronization from a shielded cable is challenging. The cable could be modified to facilitate extraction of the synchronization signal; however, that modification is not likely to be supported by the manufacturers of the ultrasound imaging equipment, and operators of medical equipment are not likely to pursue a modification not sanctioned by a manufacturer, particularly because of liability and warranty concerns. Thus, it would be desirable to provide a technique for synchronizing HIFU interference in an ultrasound image, without requiring the use of a stable synchronization signal generator as disclosed in the '867 patent. The synchronization should also be achieved without modifying an ultrasound imaging apparatus to provide a synchronization signal.

SUMMARY OF THE INVENTION

The present invention encompasses systems and methods for enabling a HIFU transducer to be synchronized to an ultrasound imaging system, to facilitate ultrasound image guided HIFU therapy. As noted above in the Background of the Invention, the '867 patent discloses that HIFU transducers can be readily synchronized to ultrasound imaging systems when the ultrasound imaging system has been modified to provide a synchronization signal. The present invention facilitates synchronization of a HIFU transducer and an ultrasound imaging system without requiring the ultrasound imaging system itself to provide a separate synchronization signal. Most commercial ultrasound imaging systems do not provide a separate synchronization signal, and as a result, implementing the synchronization technique disclosed in the '867 patent can require modifying existing ultrasound imaging systems. However, a preferred embodiment of the present invention enables gating HIFU synchronously with ultrasound imaging without requiring a customized ultrasound imaging system. An aspect of this embodiment is utilizing a HIFU transducer as a receiver, to detect scattered ultrasound waves generated by the ultrasound imaging system, so that the scattered ultrasound imaging wave received by the HIFU transducer can be used to synchronize the HIFU transducer to the ultrasound imaging system. Alternatively, a separate, dedicated receiver could be used to receive scattered ultrasound imaging waves (instead of using the HIFU transducer as a receiver); however, using the HIFU transducer as a receiver is an elegant solution. Particularly, when an ultrasound imaging transducer and a HIFU transducer are coplanar (such a configuration facilitates visualization of the treatment process), or coaxial, it is possible to use the HIFU transducer as a focused receiver to detect scattered ultrasound imaging waves from the ultrasound imaging transducer. The scattered ultrasound imaging waves received by the HIFU transducer can then be processed to provide a control signal to be used in energizing the HIFU transducer, the control signal being synchronized with the ultrasound imaging waves to reduce the amount of interference introduced into the ultrasound image by the HIFU waves.

In one embodiment, the processing of the scattered ultrasound imaging waves received by the HIFU transducer (or a dedicated receiver) is achieved using a computing device. In another embodiment, the processing of the scattered ultrasound imaging waves received by the HIFU transducer (or a dedicated receiver) is achieved by a hard-wired circuit. This approach enables synchronization to be achieved without customizing an ultrasound imaging system to provide a separate synchronization signal, and without cataloging and reproducing frame rates with a function generator (a technique that is also described in the '867 patent).

The approach described herein can be implemented whenever the ultrasound imaging transducer and the HIFU transducer are both coupled to a medium that scatters the ultrasound imaging waves. Most tissue targeted during HIFU therapy will provide sufficient scattering. Note that if a separate receiver is used to collect the scattered ultrasound imaging waves, as opposed to using the HIFU transducer to collect the scattered ultrasound imaging waves, the separate receiver will similarly need to be coupled to the medium that scatters the ultrasound imaging waves.

Another aspect of the present invention is directed to automatically determining the frame rate and phase of an ultrasound imager in real time and employing the frame rate to dynamically trigger the application of high intensity ultrasound therapy. Consequently, as a user adjusts the controls of the imager, the ultrasound therapy not only remains synchronized with the frame rate, but also remains in phase, so that the HIFU waves only obscure regions outside the area of interest in the imaging display.

BRIEF DESCRIPTION OF THE DRAWINGS FIGURES

The foregoing aspects and many of the attendant advantages of the various embodiments discussed below will become more readily appreciated as the same becomes better understood by reference to the following detailed description, when taken in conjunction with the accompanying drawings, wherein:

FIGS. 1A-1C (all depicting Prior Art) respectively illustrate ultrasonic images generated during the simultaneous use of ultrasound for imaging and therapy, the pulsing of the HIFU in a conventional scanned image, and the synchronized pulsing of the HIFU and the scan image so as to shift the noise away from a displayed treatment site;

FIG. 2 (Prior Art) is a block diagram illustrating the components of an earlier system that is capable of synchronizing HIFU therapy in ultrasound imaging, which requires the modification of commercially available ultrasound imaging equipment to achieve a synchronization signal;

FIG. 3 schematically illustrates using a therapy transducer as a receiver to detect imaging signals from an ultrasound imaging transducer, in accord with one embodiment of the present invention;

FIG. 4 is a block diagram illustrating one embodiment of the present invention, which enables an ultrasound imaging system to be synchronized with a HIFU therapy system, without requiring the ultrasound imaging system to provide a synchronization signal;

FIG. 5 graphically illustrates an exemplary voltage signal that is generated by detecting B-mode imaging signals with a HIFU transducer;

FIG. 6A schematically illustrates a basic synchronization circuit for implementing the synchronization processor of FIG. 4;

FIG. 6B schematically illustrates a basic portion of the signal conditioning performed by the synchronization circuit of FIG. 6A;

FIG. 6C and 6D graphically illustrate exemplary signals associated with the synchronization circuit of FIG. 6A;

FIG. 6E schematically illustrates an exemplary synchronization circuit used to implement the synchronization processor of FIG. 4 in one embodiment of the present invention;

FIG. 7 graphically illustrates an exemplary synchronization signal generated by the synchronization circuit of FIG. 6;

FIG. 8 is an ultrasound image in which interference from HIFU waves has been shifted to fringes of the ultrasound image, enabling a focal region of the HIFU beam to be visualized in the ultrasound image;

FIG. 9 schematically illustrates an exemplary computing system used to implement the synchronization processor of FIG. 4 in another embodiment of the present invention;

DESCRIPTION OF THE PREFERRED EMBODIMENT

Figure 1A:
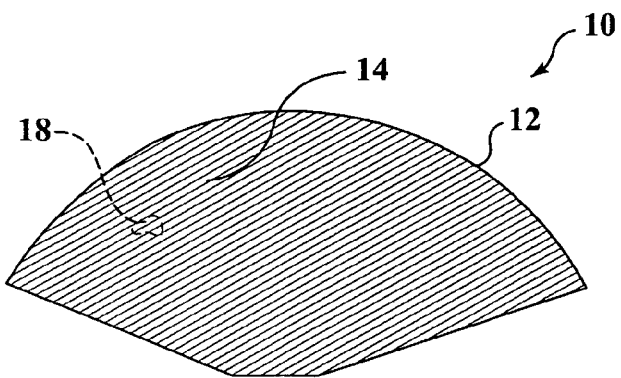
Figure 1B:
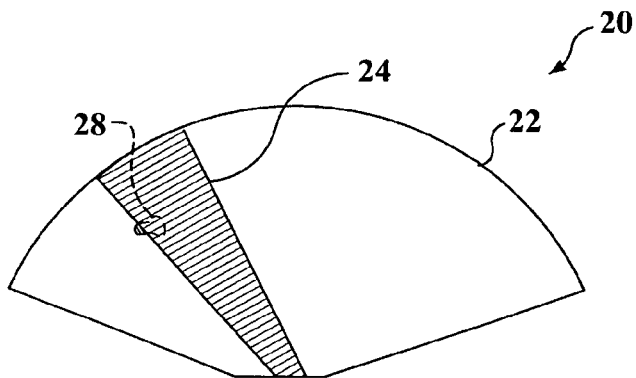
Figure 1C:
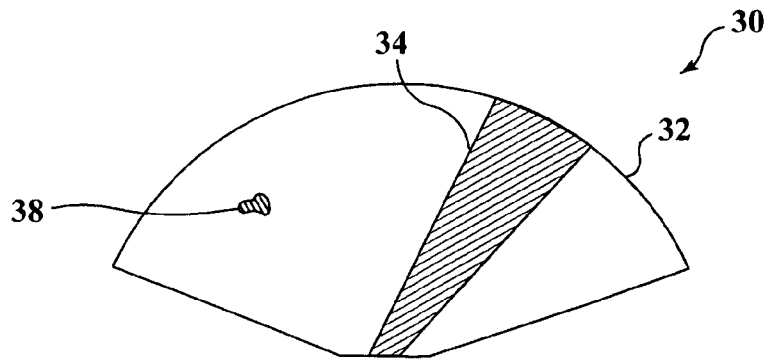
Figure 2:
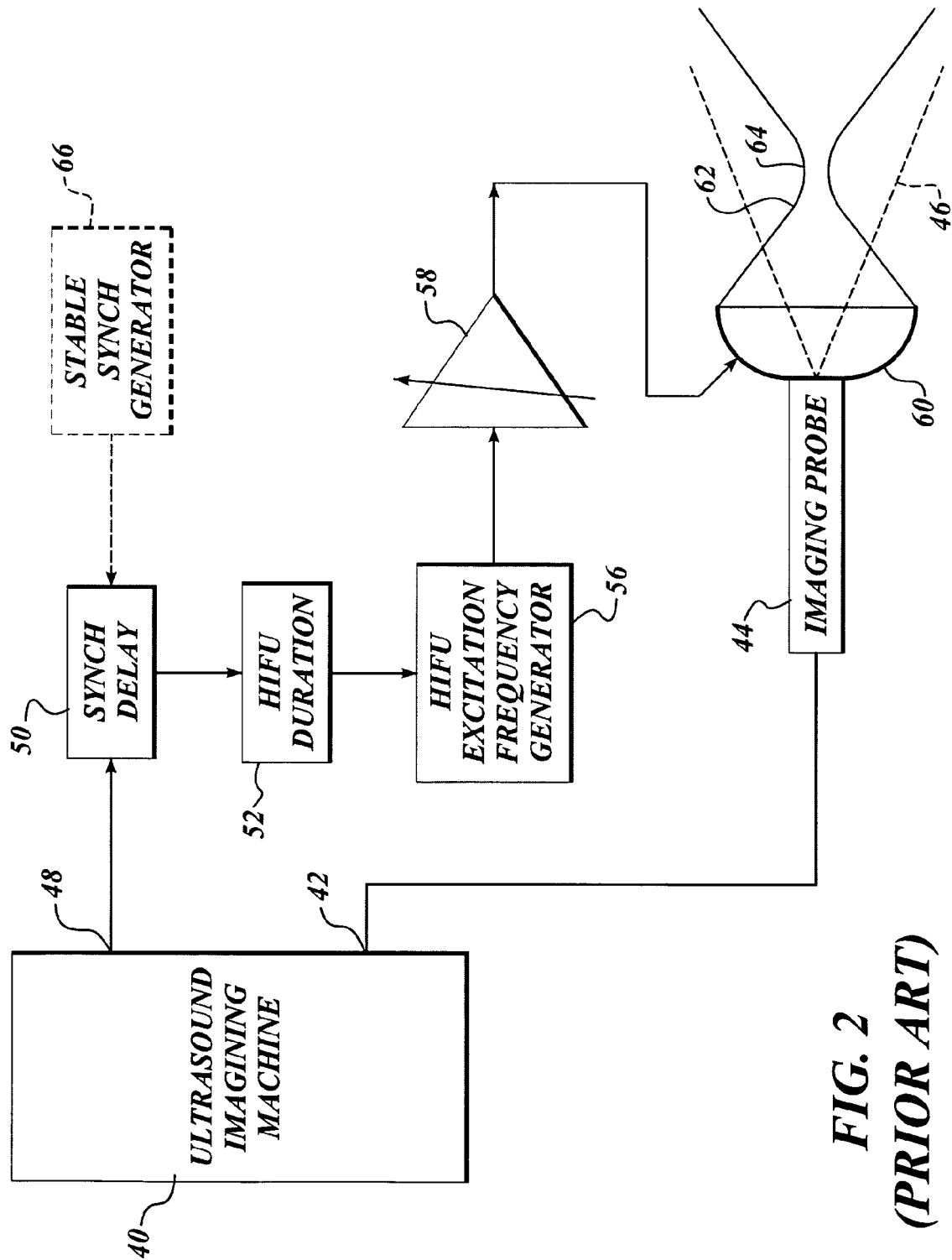

Prior art HIFU/imaging ultrasound synchronization techniques have relied on modification of the ultrasound imaging system to provide a synchronization signal to react to operator controlled adjustments, such as image depth, to maintain synchronization between the HIFU system and the ultrasound imaging system. Embodiments of the present invention facilitate HIFU/imaging ultrasound synchronization with an arbitrary, unmodified ultrasound imaging system (i.e., an ultrasound imaging system not modified to provide a synchronization signal). Empirical studies indicate that embodiments of the present invention facilitates ultrasound image guided application of HIFU using both Doppler and B-mode ultrasound imaging systems. The ability of the present invention to be used in connection with Doppler imaging is significant, as Doppler imaging is crucial for blood flow imaging. Doppler imaging has a significantly more complicated signal pattern than B-mode imaging, and synchronization of HIFU therapy with Doppler imaging requires more data to achieve stable synchronization than is required to achieve stable synchronization with B-mode imaging. Embodiments of the present invention have been successfully tested for compatibility with both Doppler imaging and B-mode imaging.

The terms "therapeutic transducer," "HIFU transducer," and "high intensity transducer," as used herein and in the claims that follow all refer to a transducer that is capable of being energized to produce ultrasonic waves that are much more energetic than the ultrasonic waves produced by an imaging transducer, and which can be focused or directed onto a discrete location, such as a treatment site in a target area. The term "HIFU beam" should be understood to refer to a characteristic pattern of HIFU waves emitted from a HIFU transducer. Ultrasound is a wave-based phenomenon; however, those of ordinary skill in the art often refer to HIFU waves as a "beam," much in the way the science of optics refers to light as a beam, even though light exhibits aspects of both waves and particles. This dual nature is particularly true with respect to HIFU waves, because HIFU waves can be focused much in the way that light can be focused (i.e., a focal point is associated with HIFU waves, and the focal point corresponds to a region where the HIFU waves are capable of delivering a maximum amount of acoustic energy).

The term "signal" is often used in the electronic arts to refer to an impulse or a fluctuating electric quantity, such as voltage, current, or electric field strength, whose variations convey information. It should be understood that as used herein, ultrasound waves, particularly ultrasound imaging waves, can be considered to be a signal. Thus, ultrasound imaging waves generated by an ultrasound imaging transducer are at times referred to in the following discussion as a signal. The term "synchronization signal," as used in the following disclosure and the claims that follow, is to be understood to mean an impulse or a fluctuating electric quantity, such as voltage, current, or electric field strength, whose variations convey information that can be used to synchronize pulses of HIFU waves with pulses of ultrasound imaging waves, so that interference from the HIFU waves in an ultrasound image generated using the ultrasound imaging waves can be reduced, or shifted to a portion of the ultrasound image that does not interfere with a particular area of interest in the ultrasound image.

To form an imaging frame, array elements in an ultrasound imaging probe transmit and receive acoustic waves according to a pattern that is determined by the manufacturer of the ultrasound imaging system. This pattern usually includes some "quiet time," during which the received signals (i.e., reflected ultrasound imaging waves) are processed by the ultrasound imaging system to generate an ultrasound image. The frame rate, which is independent of the video frame rate (often available in NTSC format through an external connector), depends on several factors, including: imaging depth, imaging modality, and the signal processing capabilities of the ultrasound imaging system.

Figure 3:
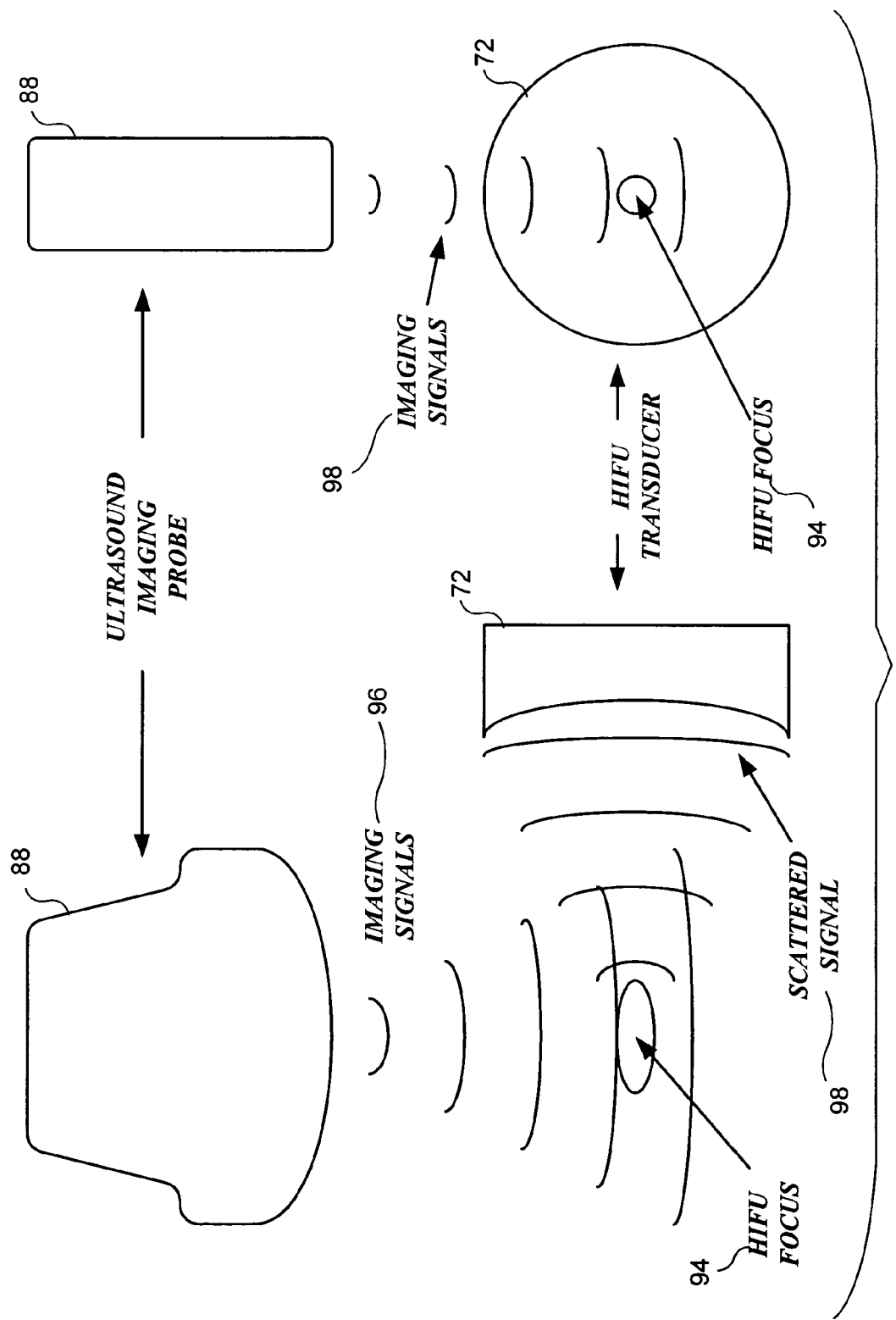

In accord with one exemplary embodiment of the present invention, a HIFU transducer can be used as a focused receiver, to detect scattered ultrasound imaging waves generated by the ultrasound imaging probe. This concept is schematically illustrated in FIG. 3. An ultrasound imaging probe 88 (including an ultrasound imaging transducer, not separately shown) produces pulses of ultrasound imaging waves 96 directed towards a target region. A HIFU transducer 72 is positioned such that a focal region 94 of the HIFU transducer lies within an image plane corresponding to ultrasound imaging probe 88 (i.e., focal region 94 lies within the path of ultrasound imaging waves 96). Some portion of the ultrasound imaging waves is reflected back towards ultrasound imaging probe 88. Those ultrasound imaging waves are used by the ultrasound imaging system to generate an ultrasound image. Another portion of the ultrasound imaging waves are reflected away from ultrasound imaging probe 88. Some portion of the ultrasound imaging waves that are reflected away from ultrasound imaging probe 88 are reflected towards HIFU transducer 72, as indicated by scattered signal 98. Because the HIFU transducer is most sensitive to imaging signals that scatter from within its focus, and since the longitudinal cross-section of the HIFU focus is small compared to the sector width of a typical diagnostic ultrasound imaging probe, the signal received by the HIFU transducer contains two types of information that can be used to achieve synchronization, including: (1) the imaging frame rate, and (2) the phasing of the imaging cycle. If the pulse repetition frequency of the HIFU burst is controlled to be equal to the imaging frame rate, then the interference will appear in the same place in each ultrasound image generated by the ultrasound imaging system. If the start of the HIFU burst is delayed from the time at which the scattered ultrasound imaging waves (i.e., scattered signal 98) are detected, then the interference will not obscure the treatment site within the ultrasound image, although a different (less critical) portion of the ultrasound image will be sacrificed (i.e., a different portion of the ultrasound image will be subject to interference from the HIFU waves).

The imaging frame rate is important for synchronization, but the value of the imaging frame rate is not used explicitly in this exemplary embodiment of the present invention. That is, the frame rate is not measured, and the value of the imaging frame rate is not used in a calculation to generate the synchronization signal that gates the HIFU burst. Because imaging signals from each imaging cycle are detected, and because the synchronization signal controlling the HIFU gating is generated in response to the detected scattered ultrasound imaging signals (i.e., scattered signal 98), the HIFU burst will be repeated at the imaging frame rate. As a result, it is not necessary to measure or specify the frame rate, and, further, the system and method employed in this technique can adapt instantly when imager settings that affect the imaging frame rate are changed. For example, when either the imaging depth or the imaging modality is changed, the imaging frame rate is also changed, but the HIFU burst will remain synchronized using the system and method of the embodiments discussed herein. Thus, a scattered ultrasound imaging signal detected with the HIFU transducer can be processed into a trigger that controls a HIFU burst that is inherently synchronized with the imaging cycle.

Note that if the HIFU transducer is positioned such that the focal region of the HIFU transducer is disposed outside of the imaging plane corresponding to the ultrasound imaging probe, it is likely that some scattered ultrasound imaging signals may still be received by the HIFU transducer. However, positioning the HIFU transducer (or a therapy probe incorporating the HIFU transducer) relative to the ultrasound imaging probe such that the focal region of the HIFU transducer does lie within the imaging plane of the ultrasound imaging probe is particularly preferred, because such an orientation will enable the focal region of the HIFU transducer to be visualized in the ultrasound image when both the ultrasound imaging transducer in the HIFU transducer are energized in a synchronized fashion. Enabling the focal region of the HIFU transducer to be visualized in an ultrasound image represents a significant benefit of the present invention.

Figure 4:
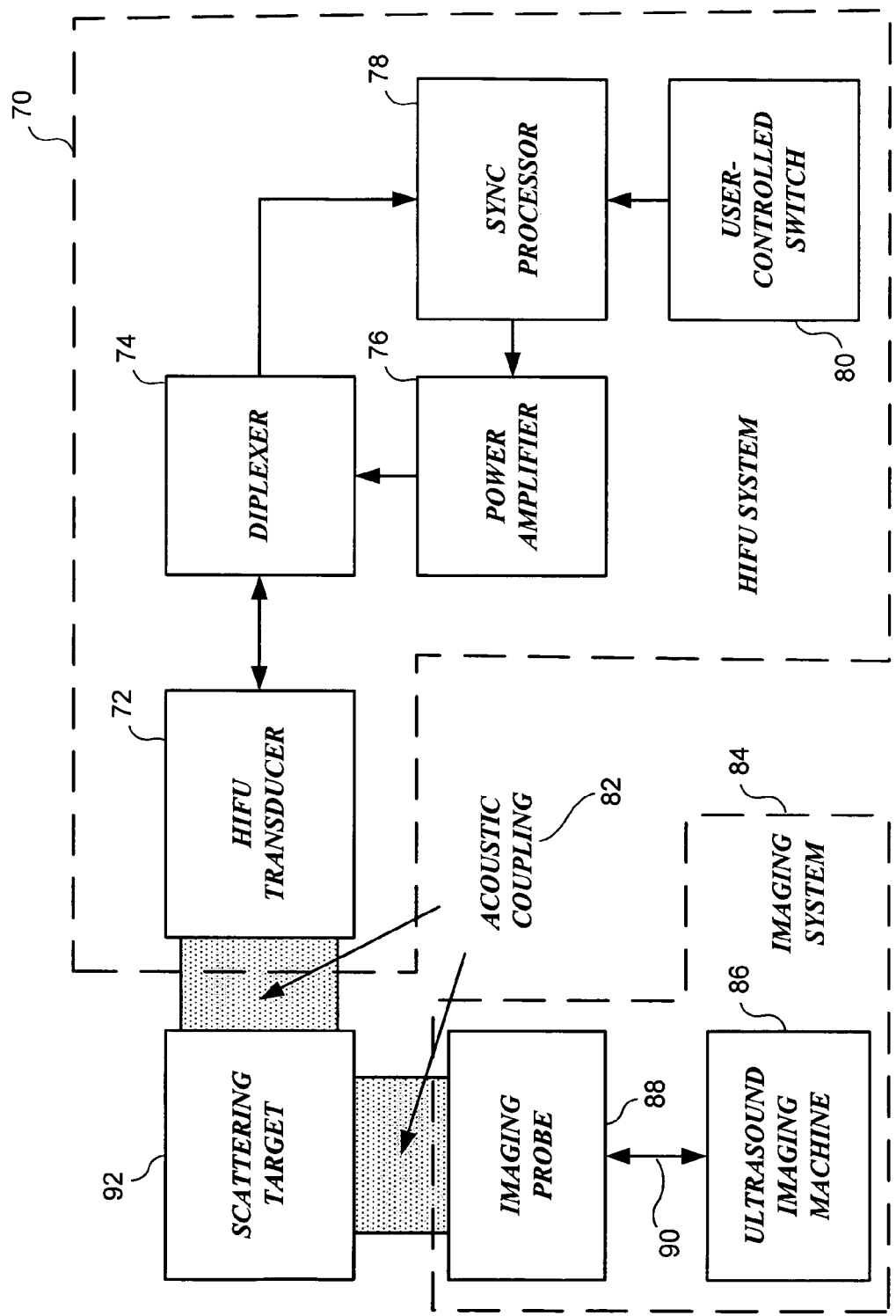

A high-level functional block diagram of one embodiment for implementing the present invention is provided in FIG. 4. As demonstrated in FIG. 4, the synchronization of a HIFU therapy system 70 with an ultrasound imaging system 84 can be achieved without requiring any electrical connection between the HIFU therapy system and the ultrasound imaging system. Significantly, all synchronization signal processing occurs outside the ultrasound imaging system, and the only information required from the ultrasound imaging system is a scattered ultrasound imaging wave (i.e., an acoustic imaging signal generated by the ultrasound imaging system, portions of which are of used by the ultrasound imaging system to generate an ultrasound image). While in one preferred embodiment (the embodiment schematically illustrated in FIG. 4) the signal processing occurs within the HIFU system, it should be understood that signal processing could alternatively occur externally of the HIFU system, based on a scattered ultrasound imaging wave generated by the ultrasound imaging system and collected by the HIFU system. That is, in an alternative embodiment, the HIFU system could be logically coupled with a processor configured to generate a synchronization signal used to gate HIFU bursts based on scattered ultrasound imaging waves generated by the ultrasound imaging system and collected by the HIFU transducer. Thus, while the embodiment schematically illustrated in FIG. 4 represents one preferred embodiment, it should be understood that FIG. 4 is not intended to limit the invention, particularly because the synchronization processor could be implemented as a component not contained within the HIFU system. Of course, where the HIFU transducer is used to collect the scattered ultrasound imaging signals to be processed to generate a synchronization signal, the HIFU transducer will be logically coupled to the synchronization processor, even if the synchronization processor is implemented outside of the HIFU system.

The synchronization can be achieved by using HIFU transducer 72 as a receiver, to detect scattered ultrasound imaging waves signals generated by an ultrasound imaging transducer (not separately shown) that is included in an ultrasound imaging probe 88. The synchronization enables the ultrasound imaging system to be operated continuously, while noise corresponding to HIFU waves is shifted away from a region of interest within an ultrasound image produced by ultrasound imaging machine 86.

Note that ultrasound imaging system 84 is intended to represent conventional and commercially available ultrasound imaging systems. Such conventional ultrasound imaging systems include an imaging probe (i.e., imaging probe 88) that generates ultrasound imaging waves, which propagate from the imaging probe to the target area. Such ultrasound imaging waves are reflected by structure and tissue within the body. Some of the reflected ultrasound imaging waves are then received by the imaging probe. An electrical signal produced by the imaging probe in response to the reflected ultrasound imaging waves is communicated to the ultrasound imaging machine (i.e., ultrasound imaging machine 86) through a cable (i.e., cable 90) and processed to provide a visual representation of the structure and tissue that reflected the ultrasonic imaging pulses. Many ultrasound imaging machines include an integrated monitor for display of the ultrasound image, or a separate monitor (not separately shown) can be employed. Significantly, FIG. 4 represents a HIFU system that can be used with any arbitrary ultrasound imaging system (i.e., the ultrasound imaging system employed does not need to be modified to provide a synchronization signal used to drive the HIFU system).

When ultrasound imaging systems are used to generate an ultrasound image of an internal treatment site in a patient, an acoustic coupling is frequently disposed in between the ultrasound imaging probe and the patient's skin layer, to enhance the acoustic coupling of the ultrasound imaging waves to the patient's tissue. Many different types of acoustic couplers can be used, including coupling gels and semi solid hydrogel-based couplers. Referring to FIG. 4, an acoustic coupling 82 is preferably employed to acoustically couple imaging probe 88 to a scattering target 92. In general, scattering target 92 will be a patient (i.e., biological tissue), because one of the most widespread applications of ultrasound image guided HIFU is for medical therapy, although it should be understood that the present invention is not limited to the synchronization of HIFU with ultrasound imaging solely in a medical context. The same principles disclosed herein could be used to simultaneously image and apply HIFU to other types of scattering targets (i.e., scattering targets other than biological tissue). Indeed, empirical studies have been performed using ultrasound imaging systems and HIFU systems corresponding to FIG. 4, wherein the scattering target employed was not biological tissue. Empirical studies have been performed using a gel tissue phantom, whose properties generally correspond to those of human tissue, to provide empirical data that were used to confirm the suitability of the synchronization method and apparatus of the present invention for use in medical therapy involving human tissue. Such results have been encouraging. The synchronization method and apparatus of the embodiments of the present invention discussed herein can be employed with many different types of scattering targets, so long as the scattering target is capable of scattering ultrasound imaging waves. Therefore, while the embodiments of the synchronization method and apparatus that have been developed are particularly well-suited for use in medical applications, they may be applicable to industrial or other non-medical applications as well, and the present invention is not limited to use in a medical context. Furthermore, while the use of the coupling agent is preferred, coupling agents are not required, so long as the ultrasound imaging transducer in imaging probe 88 and HIFU transducer 72 can be sufficiently acoustically coupled with scattering target 92.

HIFU system 70 includes HIFU transducer 72, a diplexer 74, a power amplifier 76, a synchronization processor 78, and a user control switch 80. As noted above, synchronization processor 78 could be implemented externally of HIFU system 70, so long as any external synchronization processor is logically coupled to power amplifier 76 to provide a synchronization signal for energizing HIFU transducer 72, so that HIFU bursts are synchronized with the ultrasound imaging system's image frame rate. When both the imaging probe and HIFU transducer are acoustically coupled to scattering target 92, the HIFU transducer can receive scattered ultrasound imaging waves, so long as the relative orientations of imaging probe 88 and HIFU transducer 72 are such that some scattered ultrasound imaging waves reach HIFU transducer 72. Empirical studies have indicated that a HIFU transducer can receive scattered ultrasound imaging waves when both the HIFU transducer and the ultrasound imaging transducer generating the ultrasound imaging waves are acoustically coupled to the same scattering target, and the HIFU transducer and the ultrasound imaging transducer are generally coplanar, or coaxial. Empirical studies have also indicated that disposing the HIFU transducer and the ultrasound imaging transducer at a spatial orientation of about 90° relative to each other can facilitate enabling the HIFU transducer to receive scattered ultrasound imaging waves. It should be understood, however, that such a spatial orientation is intended to be exemplary, rather than limiting, and that other spatial orientations are possible, so long as the HIFU transducer is positioned to receive at least some scattered ultrasound imaging waves.

Functionally, acoustic waves (i.e., ultrasound imaging waves 96 as illustrated in FIG. 3) from ultrasound imaging probe 88 scatter within the HIFU focus (i.e., focal region 94 as illustrated in FIG. 3) in scattering target 92, resulting in scattered signal 98 (see FIG. 3) that is received by HIFU transducer 72, generating a voltage signal (not separately shown) at HIFU transducer 72, which is routed to synchronization processor 78 through diplexer 74. The function of the diplexer is to ensure that signals received from the HIFU transducer are directed only to synchronization processor 78, and that signals from power amplifier 76 are directed only to the HIFU transducer. In a working prototype, the diplexer was implemented using a T/R switch (Ritec, Inc. Model RDX-6™) designed for pulse/receive systems. Those of ordinary skill in the art will recognize that diplexers are relatively simple devices, which any electrical engineering student is able to construct. Note that a diplexer would not be needed if a stand alone, dedicated receiver were used to collect the scattered ultrasound imaging signals. Such an embodiment is described below. A diplexer, or any other device that routes collected scattered ultrasound imaging signals to the synchronization circuit and power signals to the HIFU transducer, should be used when the HIFU transducer is used as a receiver to collect the scattered ultrasound imaging signals used by the synchronization circuit.

In response to each imaging cycle (based on scattered ultrasound imaging waves received by the HIFU transducer), the synchronization processor produces a tone burst at the HIFU frequency. When the user-controlled switch is closed, the tone burst serves as input to the power amplifier. The power signal is routed to the HIFU transducer through the diplexer and generates a burst of HIFU within the scattering target. Details of the detected signal and the synchronization processor are described below.

With respect to synchronization processor 78, empirical testing has confirmed that synchronization processor 78 can be implemented using a computing system combined with software configured to generate a synchronization signal based on scattered ultrasound imaging signals received by the HIFU transducer, as well as being implemented using a custom-designed application-specific circuit that similarly generates a synchronization signal based on scattered ultrasound imaging signals received by the HIFU transducer. While both approaches provided empirical data indicating that either approach is functional, the use of a custom-designed circuit is particularly elegant, in that such a circuit can be readily implemented as a component to add into existing HIFU systems, or incorporated into future HIFU systems. In particular, while computing devices are relatively ubiquitous, the custom-designed circuit can be fabricated at a relatively low-cost, and may even be price competitive with the cost of software which would be required to facilitate the implementation of synchronization processor 78 using a computing system.

Figure 5:
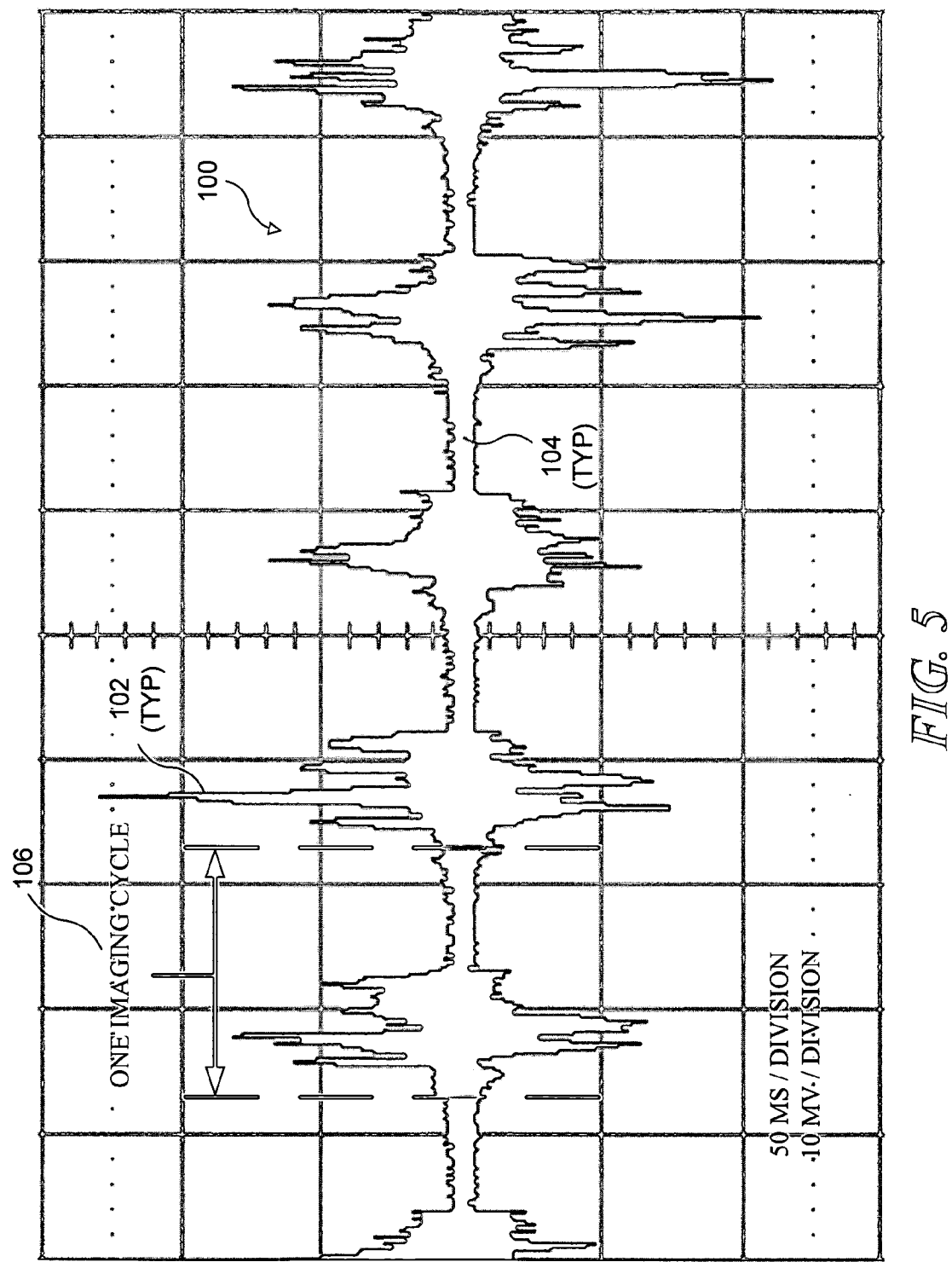

FIG. 5 graphically illustrates an exemplary voltage signal 100 generated by detecting scattered B-mode imaging signals with a HIFU transducer. Voltage signal 100 is periodic, and there is a clear discrepancy between higher amplitude portions 102 and lower amplitude portions 104. Two properties of voltage signal 100 were considered when designing an analog circuit to implement synchronization processor 78 (i.e., to implement a logic-level trigger for controlling HIFU transducer 72). First, the amplitude of the exemplary voltage signal is on the order of about 1 mV, and therefore, the voltage signal must be amplified before being used. Second, the larger amplitude sections (i.e., portions 102) are based on zero-mean sinusoidal pulses transmitted by separate array elements in the ultrasound imaging probe. Each pulse is only a few cycles of a frequency that is about 1 MHz (most B-Mode ultrasound imaging systems transmit ultrasound in the range of 3-11 MHz), so the pulse length is less than a few microseconds. The higher amplitude pulses are separated by periods of zero amplitude (i.e., portions 104) that last for hundreds of microseconds, during which the ultrasound imaging system is collecting echo data. Empirical studies have shown that a logic-level trigger can be generated reliably by amplifying voltage signal 100, averaging the high amplitudes portions (i.e., portions 102), and then applying a voltage threshold to eliminate amplitudes that might represent noise and should be excluded.

Figure 6A:
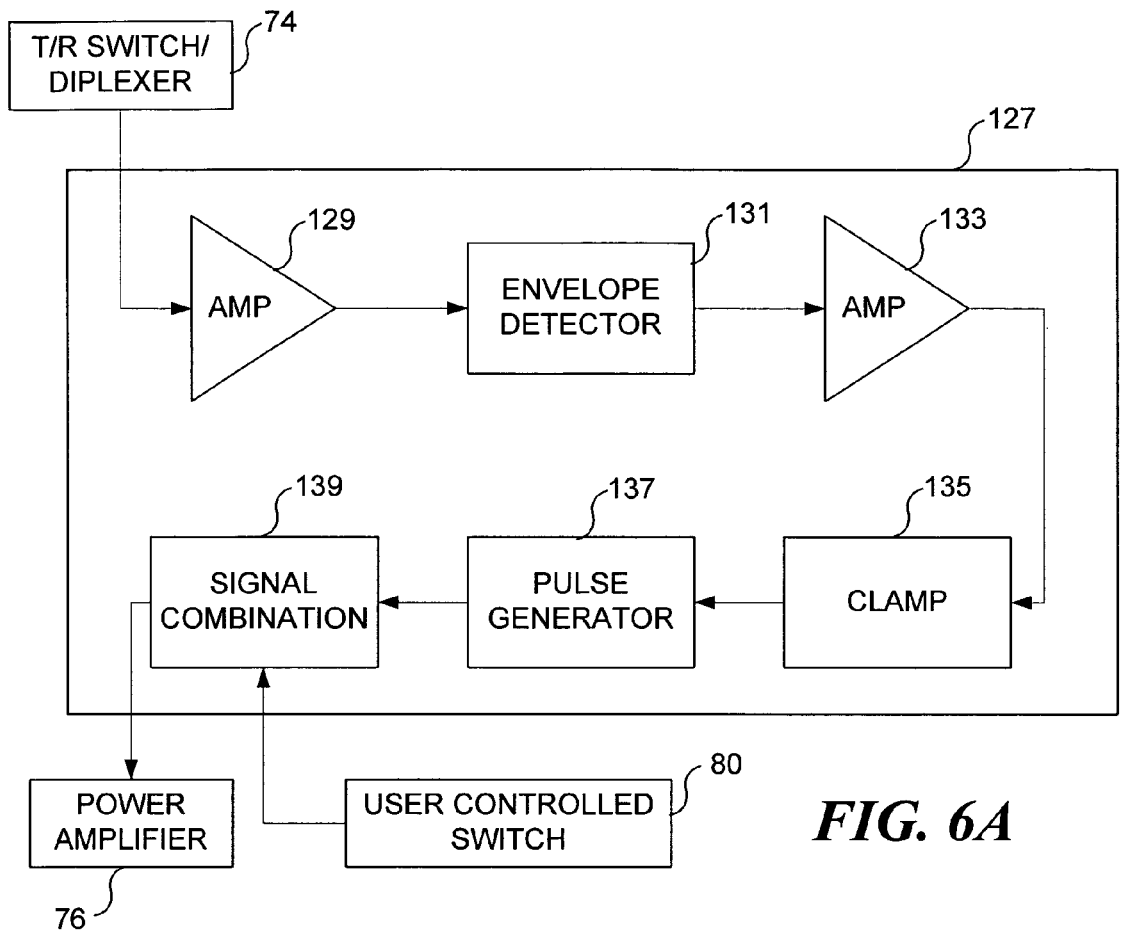
Figure 6B:
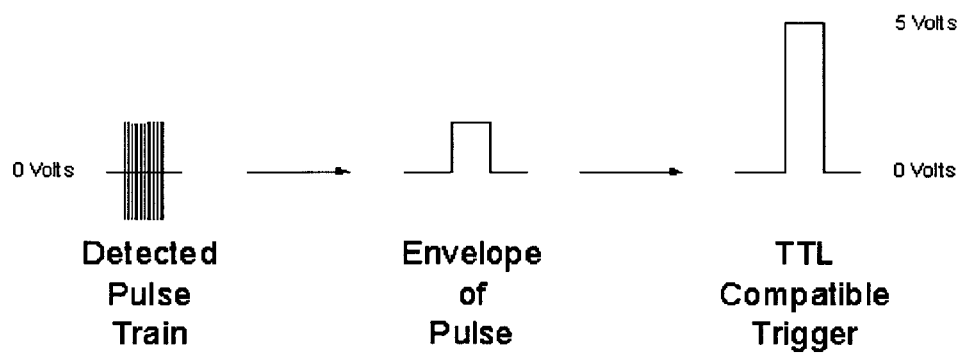
Figure 6C:
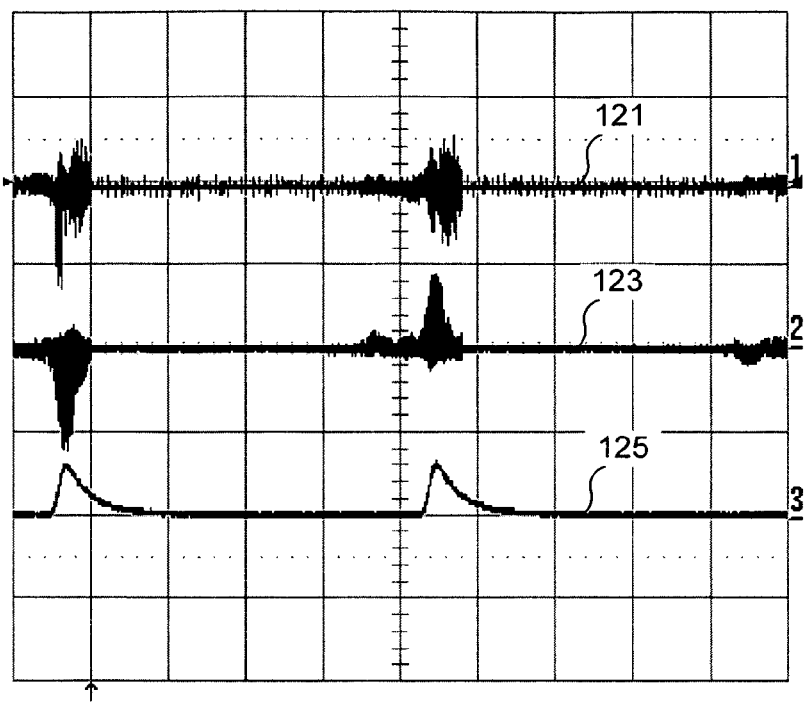

FIG. 6A schematically illustrates a basic synchronization circuit 127 for implementing the synchronization processor of FIG. 4. FIG. 6B schematically illustrates a basic portion of the signal conditioning performed by the synchronization circuit of FIG. 6A, detecting a pulse train, determining an envelope of the pulse, and generating a trigger signal that is compatible with any digital circuitry operating between 0 and 5 volts. Of course, the synchronization circuit can be modified to be compatible with digital circuitry operating at any other voltage level. Synchronization circuit 127 is configured to amplify voltage signal 100 (FIG. 5), averaging the high amplitude portions (i.e., portions 102), and applying a voltage threshold to eliminate amplitudes that might represent noise, generally as described above. Synchronization circuit 127 receives an input signal (i.e., voltage signal 100 of FIG. 5) from diplexer 74 (FIG. 4) and includes a first amplifier 129 for amplifying the input voltage signal, which (representing scattered ultrasound imaging waves detected by the HIFU transducer) is generally of insufficient magnitude for signal processing without amplification. The output of first amplifier 129 is coupled to an envelope detector 131, which is configured to average the amplified signal received from first amplifier 129. The output of envelope detector 131 is coupled to a second amplifier 133, because the averaging function performed by the envelope detector reduces the signal voltage level. FIG. 6C graphically illustrates an input signal 121 received from diplexer 74, an output signal 123 from first amplifier 129, and an output signal 125 from envelope detector 131. With respect to output signal 125, a better trigger signal is achieved when the rising edge of signal has a steep slope.

Referring again to FIG. 6A, the output of second amplifier 133 is directed to a clamp 135, which is configured to ensure that a maximum signal output directed to downstream circuit elements does not exceed a maximum voltage that can be tolerated by the downstream circuit elements. In at least one embodiment, clamp 135 limits the signal voltage passed on to downstream circuit elements to a maximum of 5.5 V. It should be understood that such a value is exemplary, and the maximum value is simply a function of the voltage that can be tolerated by specific circuit elements employed downstream of clamp 135. Therefore, the value of 5.5 V is not intended to limit the invention. Output from clamp 135 represents a logic level trigger achieved by processing the scattered ultrasound imaging signal detected with the HIFU transducer. The remaining portion of synchronization circuit 127 is dedicated to generating logic signals that control the phasing and gating of the HIFU burst. The output of clamp 135 is directed to a pulse generator 137 (preferably implemented using a timing chip) to create control signals for the HIFU burst in response to signal output (i.e., the trigger output) from clamp 135.

Figure 6D:
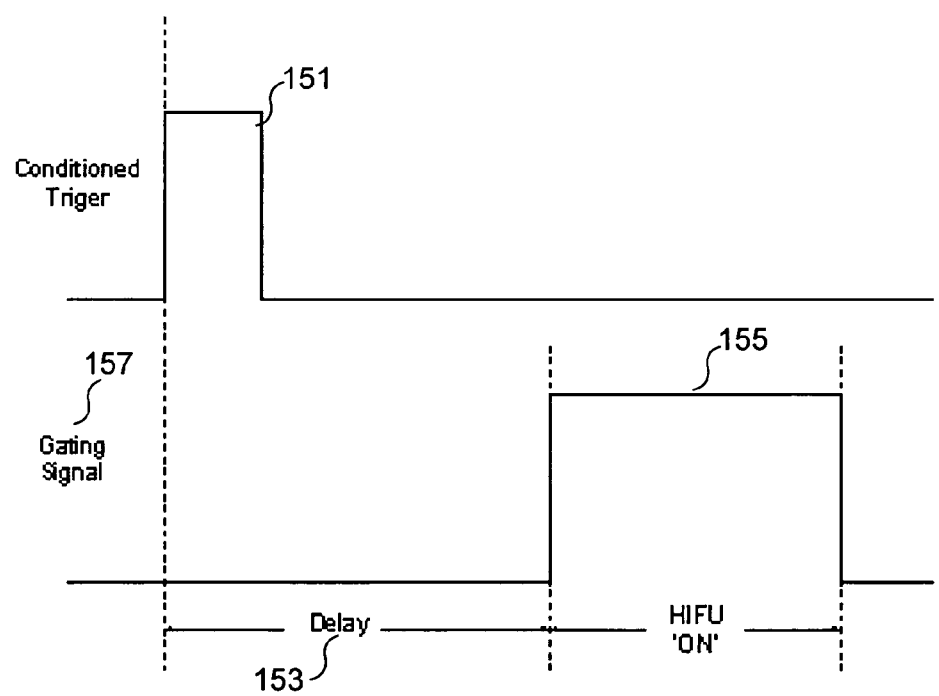

Referring to FIG. 6D, each pulse peak in output signal 125 corresponds to a conditioned trigger 151 (indicating that the ultrasound imaging system is emitting and collecting ultrasound imaging pulses for an image frame). If the HIFU pulse was initiated such that it coincided with the conditioned trigger (i.e., with a pulse corresponding to an ultrasound imaging pulse), the resulting ultrasound image would be saturated with noise from the HIFU pulse. Thus, in synchronization control signal 157 output by pulse generator 137, a delay 153 must separate a HIFU ON pulse 155 from the conditioned trigger (i.e., the ultrasound imaging pulses). Pulse generator 137 generates a synchronization signal that can be used to gate the HIFU pulses so that a delay separates the HIFU pulses from the conditioned trigger. Preferably, both the duration of the delay and the duration of the HIFU pulse are adjustable. The delay begins with the rising edge of the clamp output, and the HIFU ON pulse begins when delay ends. The HIFU ON pulse ends before next imaging cycle begins. Note that each HIFU excitation is a response to an imaging burst.

Referring again to FIG. 6A, it should also be understood that the HIFU transducer is not actually being energized during each HIFU ON pulse. If the user-activated control switch (i.e., user-controlled switch 80 of FIG. 4) is not in an ON position (indicating that the user has requested that the HIFU transducer be energized), then the HIFU transducer will not be energized even during a HIFU ON pulse. Energizing the HIFU transducer only during a HIFU ON pulse when the user-controlled switch is also in the ON position is achieved by signal combination element 139 of synchronization circuit 127, which combines signals from pulse generator 137 and user-controlled switch 80. Signal combination element 139 will provide a synchronization control signal to the power amplifier energizing the HIFU transducer (i.e., power amplifier 76 of FIG. 4) only when a HIFU ON pulse received from the pulse generator 137 coincides with a power amplifier ON signal being received from user-controlled switch 80. No synchronization control signal will be provided to the power amplifier by the signal combination element during either of the two following conditions: (1) no power amplifier ON signal is being received from the user-activated switch; and (2) no HIFU ON pulse is being received from pulse generator 137.

Figure 6E:
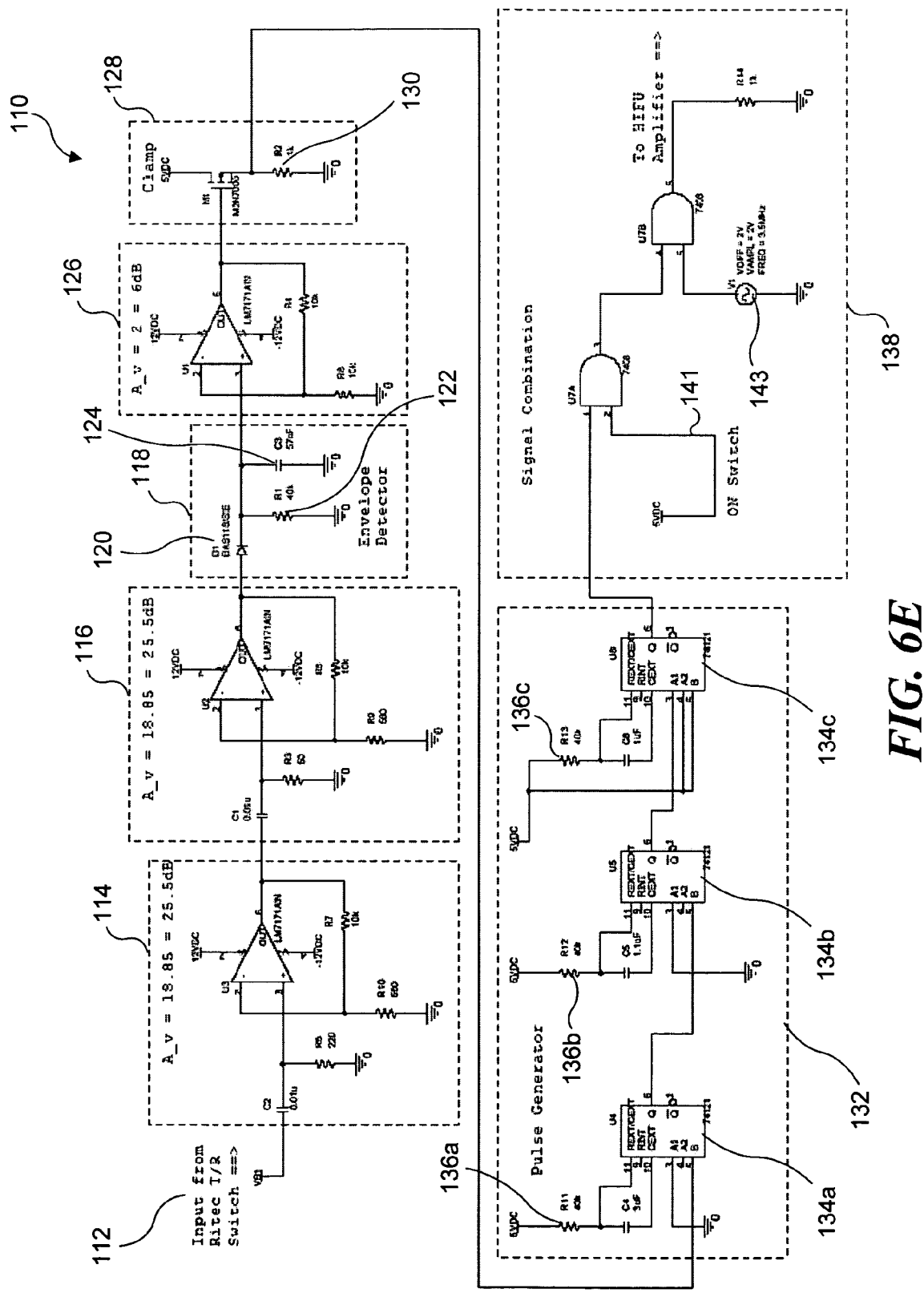

Having described synchronization circuit 127 in general functional terms, a more detailed description of an exemplary synchronization circuit 110, utilized in an exemplary working prototype of the embodiment, will be provided. FIG. 6E schematically illustrates exemplary synchronization circuit 110, designed to implement synchronization processor 78. Synchronization circuit 110 is configured for amplifying voltage signal 100 (FIG. 5), averaging the high amplitudes portions (i.e., portions 102), and applying a voltage threshold to eliminate amplitudes that might represent noise, generally as described above. It should be understood that while synchronization circuit 110 represents a preferred embodiment of the present invention, synchronization circuit 110 represents but one of many different circuits that could be used to implement synchronization processor 78 of FIG. 4. Furthermore, while averaging the high amplitude portions of voltage signal 100 represents a particularly preferred processing technique implemented by synchronization circuit 110, it should be understood that other synchronization circuits can be employed that do not necessarily average the high amplitude portions of voltage signal 100. While such averaging appears to facilitate achieving a more reliable synchronization circuit, it is not clear that averaging is a necessary step in implementing this embodiment. Thus, synchronization circuit 110 is intended to be exemplary, rather than limiting.

Synchronization circuit 110 receives an input signal 112 (i.e., voltage signal 100 of FIG. 5) from diplexer 74 (FIG. 4). Synchronization circuit 110 includes a first amplifier 114 and a second amplifier 116, for amplifying input signal 112 (i.e., voltage signal 100). Each amplifier is based on a non-inverting operational amplifier (National Semiconductor, type LM7171™) and has a gain of about 25 dB. The non-inverting input to each amplifier is AC coupled with a series capacitor and grounded through a low impedance resistor. The two RC pairs form a high-pass filter ($f_c$=318 kHz) that blocks low frequency noise. Grounding the input node of each amplifier through a low impedance reduces noise in the circuit when a signal is not being applied to the amplifier. Input signal 112 is received and amplified by first amplifier 114. The output of first amplifier 114 is received and amplified by second amplifier 116. The output of second amplifier 116 is directed to envelope detector 118. Multiple amplifiers are used to increase the overall gain at higher frequencies.

Envelope detector 118 is configured to rectify the output of second amplifier 116 with a series diode 120 and routes the rectified output to a resistor 122 that is connected to ground in parallel with a capacitor 124. The capacitor is an integrator that stores charge from the amplified pulses that are detected with the HIFU transducer (i.e., from the output of second amplifier 116). When resistor 122 in envelope detector 118 is implemented with a potentiometer (R1 in FIG. 6E), the RC time constant can be selectively tuned by adjusting the resistance such that the output voltage of envelope detector 118 replicates the positive voltage envelope of voltage signal 100 (FIG. 5) after amplification. This capability enables implementation of the averaging step previously noted, where multiple pulses are combined for thresholding. The output of envelope detector 118 is then coupled to a third amplifier 126.

Third amplifier 126, which can be implemented using a non-inverting operational amplifier (e.g., a National Semiconductor, type LM7171™) with about 6 dB of gain, amplifies the output of envelope detector 118. The third amplifier is included in synchronization circuit 110 to counteract the voltage drop across diode 120 in the envelope detector. The output of third amplifier 126 is coupled to a clamp 128.

Clamp 128 is implemented in this embodiment using an n-channel metal oxide semiconductor field effect transistor (MOSFET) (e.g., an ON Semiconductor, type 2N7000™), to threshold the output from third amplifier 126. Signals above 1.7 V that are received from third amplifier 126 will generate a logic-level output (5 V maximum) across a source resistor 130 (R2 in FIG. 6E). The clamp also protects circuit elements downstream, which can tolerate a maximum input of 5.5 V. Output from clamp 128 represents a logic level trigger achieved by processing the scattered ultrasound imaging signal detected with the HIFU transducer. The remaining portion of synchronization circuit 110 is dedicated to generating logic signals for controlling the phasing and gating of the HIFU burst.

Figure 7:
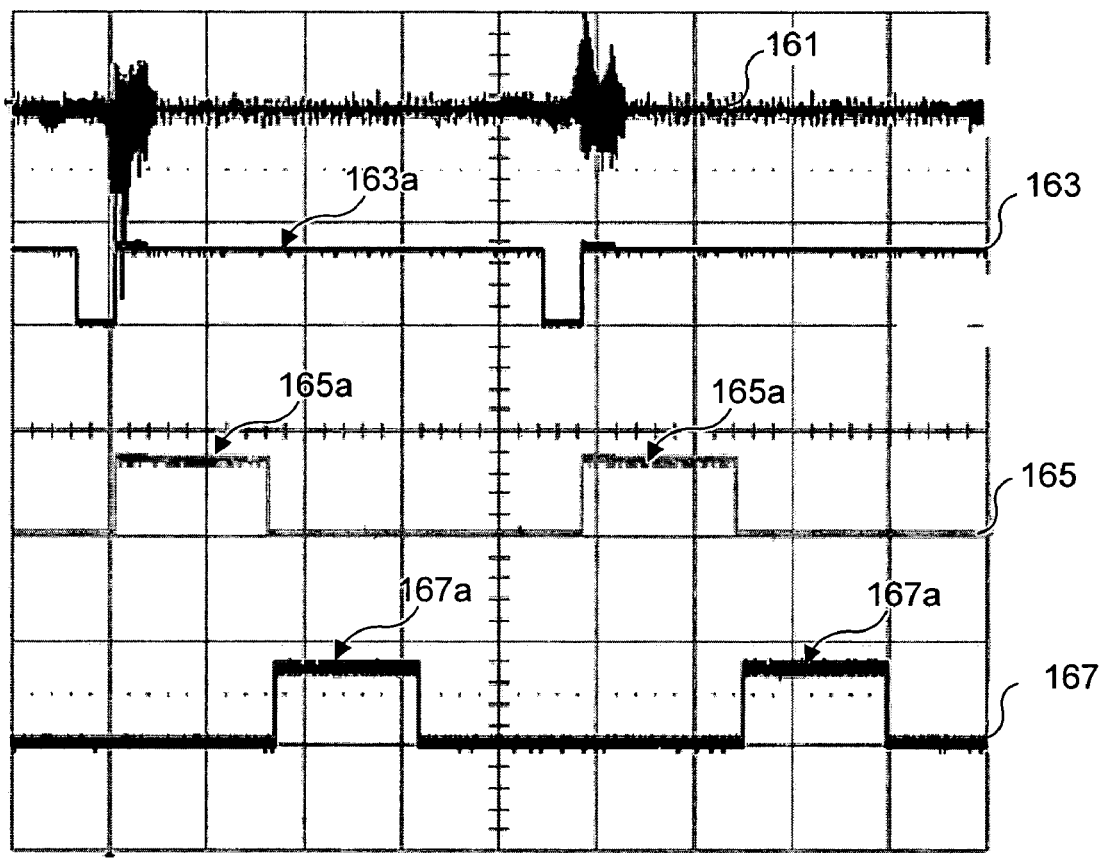

The output of clamp 128 is directed to a pulse generator 132, implemented using mono-stable multi-vibrator timing chips 134a, 134b, and 134c (e.g., Texas Instruments, type SN74121™). The timing chips are used to create control signals for the HIFU burst in response to signal output (i.e., the trigger output) from clamp 128. The output from each timing chip is a logic-level pulse whose duration is controlled by an RC time constant. Potentiometers 136a, 136b, and 136c can be used in place of fixed resistors, so that the pulse lengths are selectively adjustable. In an initial prototype, only two timing chips (timing chips 134b and 134c) were employed, including one for a phase delay and one to gate the HIFU burst. However, it was determined that because diplexer 74 (shown in FIG. 4) is not a perfect transmit/receive switch, a small fraction of the signal from the power amplifier is routed to the synchronization circuit (i.e., the initial prototype of synchronization circuit 110, which included only two timing chips in pulse generator 132) during a HIFU burst. Thus, the initial exemplary embodiment prototype with only two timing chips processed a small fraction of the signal from the power amplifier as if it were scattered ultrasound imaging signals detected by the HIFU transducer, and a "false trigger" resulted. The addition of timing chip 134a upstream of the original two timing chips (i.e., timing chips 134b and 134c) solved the false trigger problem. The timing chips feature inputs that are independent from their outputs through the duration of an output pulse. That is, an output pulse cannot be initiated until the previous output pulse is complete. Thus, as long as the output pulse of the first chip (timing chip 134a) is longer than the sum of the output pulses from the second and third chips (timing chips 134b and 134c), which occur sequentially, the false trigger will be ignored by the first timing chip. Exemplary signals generated by pulse generator 132 are shown in FIG. 7. Signal 161 is an input from T/R switch/diplexer 74, signal 163 is the output of timing chip 134a, signal 165 is the output of timing chip 134b, and signal 167 is the output of timing chip 134c.

An exemplary method of adjusting the delay and duration of the HIFU will now be described. It should be recognized that the exemplary method is not intended to limit the invention, and those of ordinary skill in the art will recognize that other methods can be used to achieve similar results. In a working prototype, control knobs were incorporated into pulse generator 132 to enable the user to adjust the delay discussed above. Referring to FIGS. 6E and 7, a first knob was logically coupled with timing chip 134a to control a duration of a pulse 163a. As indicated above, so long as pulse 163a is longer in duration than the sum of the duration of an output pulse 165a (from timing chip 134b) and an output pulse 167a (from timing chip 134c), any false trigger will be ignored by the first timing chip. Pulse 163a is initiated by the enveloped version of line 161 (i.e., the signal input from T/R switch/diplexer 74, after it has been processed by the envelope detector, amplifier and clamp portions of the synchronization circuit). The duration of pulse 163a can be adjusted by the user manipulating the control knob logically coupled with timing chip 134a, which protects against false triggers from the HIFU itself, since no received signal within this window will trigger the HIFU. Pulse 165a is also triggered by the enveloped version of line 161. The duration of pulse 165a can be user-adjusted by manipulating a control knob logically coupled with timing chip 134b. The end of pulse 165a triggers timing chip 134c to pass the HIFU signal. The HIFU will be on (provided the user-controlled switch is actuated) for the duration of pulse 167a. The duration of pulse 167a can be user adjusted by manipulating a control knob logically coupled with timing chip 134c. While the exemplary implementation employed adjustable analog radio-dial style knobs, it should be recognized that other user interface implementations are possible. For example, users could enter values into a software program (running on a personal computer, an ASIC, or microprocessor) that controls the synchronization.

Figure 8:
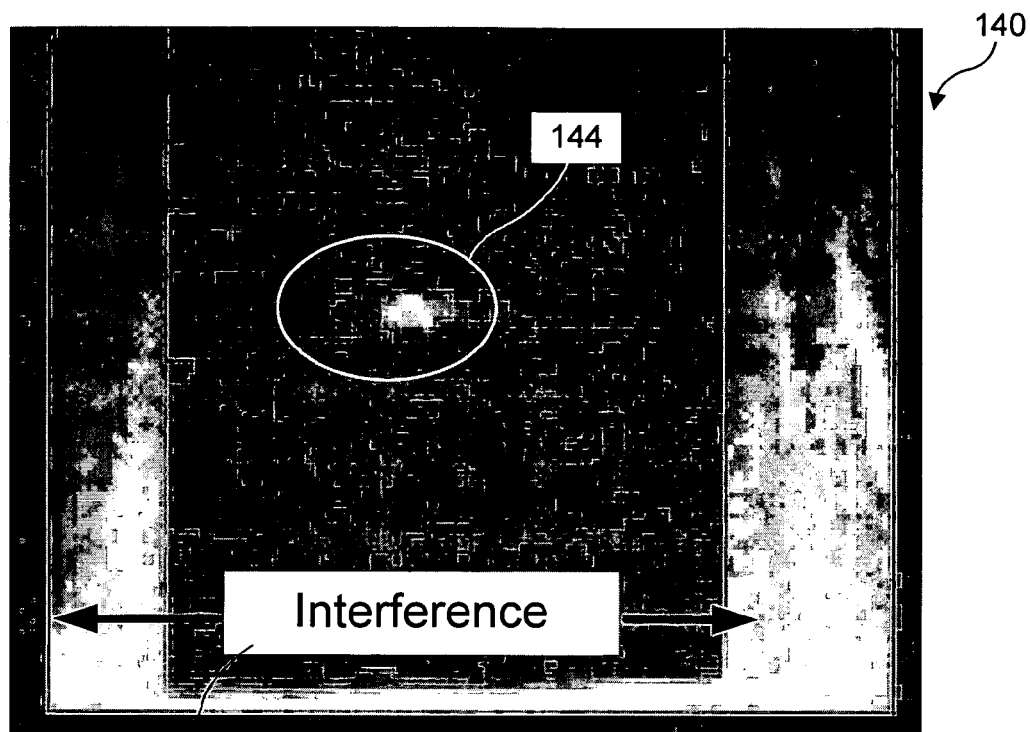

Thus, timing chips 134a, 134b, and 134c are triggered consecutively, which allows pulses 165a and 167a to be generated during a non-retriggerable period (i.e.; during each pulse 163a), thereby preventing false triggers. The rising edge of output signal 125 (see FIG. 6C) triggers timing chip 134a. The rising edge of pulse 163a (the output from timing chip 134a) triggers timing chip 134b. The falling edge of pulse 165a (the output from timing chip 134b) triggers timing chip 134c. Finally, timing chip 134c produces pulse 167a. Referring to the pulses graphically illustrated in FIG. 7, when signal 163 transitions from a low amplitude to a high amplitude (i.e.; the initiation of each pulse 163a), pulses 165a and 167a are generated automatically. Further, the generation of pulses 165a and 167a can only be triggered by a low amplitude to high amplitude transition in signal 163 (i.e.; at the initiation of each pulse 163a, not at the termination of each pulse 163a). FIG. 8 is an ultrasound image 140 that can be used to relate the output signal from pulse generator 132 to an ultrasound image. The duration of the phasing pulse determines the location of interference 142 on the ultrasound image relative to a HIFU focal region 144. Adjusting the length of the phase delay moves the interference to the left or to the right on the image, and, as shown in FIG. 8, the interference can be relegated to the sides of the ultrasound image.

The length of the gating pulse determines the total area of interference on the image. The area of interference will increase as the burst length increases.

Referring once again to synchronization circuit 110 of FIG. 6E, the output of pulse generator 132 is directed to a signal combination element 138, implemented using an AND logic chip (e.g., Texas Instruments, type SN7408™), which combines the gating pulse (i.e., the output of pulse generator 132) with a local oscillator signal (using, for example, a Linear Technologies, type LTC1799™ oscillator), and output 141 from a user-controlled switch. Because the synchronization circuit produces a tone burst in response to every imaging cycle, the user-controlled switch ensures that HIFU bursts are only transmitted to the target when desired. When HIFU is switched "ON" by the user (with user-controlled switch 80 of FIG. 4), a tone burst at the HIFU frequency is sent to power amplifier 76, which is used to energize HIFU transducer 72 (see FIG. 4). In a working exemplary embodiment prototype, a Class-D amplifier specifically developed for use with portable HIFU systems was used to implement power amplifier 76. As noted above, the power signal is routed to the HIFU transducer through diplexer 74, thereby completing the signal processing loop.

Figure 16A:
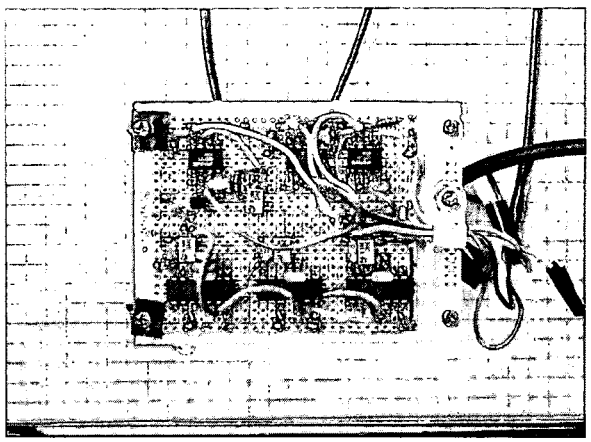
FIGS. 16A-16C illustrate an exemplary working prototype of a synchronization circuit.
Figure 16B:
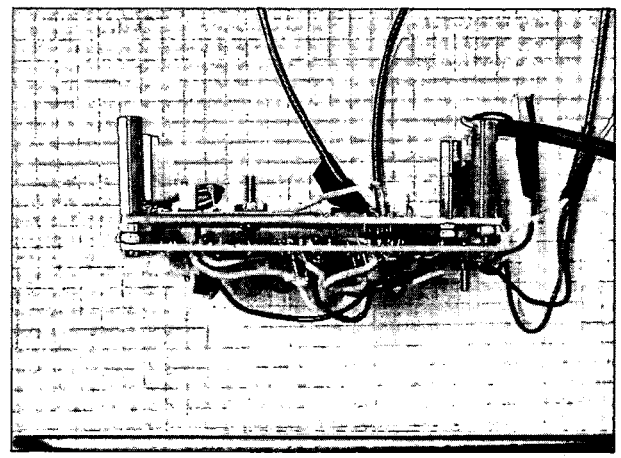
Figure 16C:
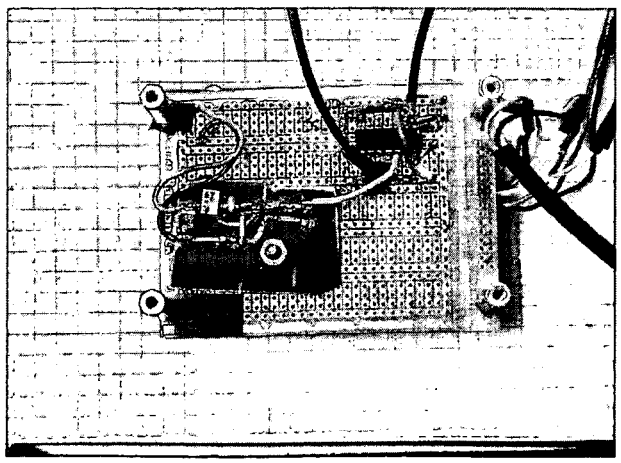

A working embodiment of synchronization circuit 110 was built with through-hole components on one side of a solderable bread board. The resulting synchronization circuit occupied 160 cm$^2$ of circuit board area, which is small compared to the size of the ultrasound imaging system and other components in the HIFU system. With surface-mount components placed on both side of a custom, 4-layer printed circuit board design, the size as synchronization circuit 110 could be reduced significantly. FIG. 16A is an image illustrating the top of an exemplary working embodiment, FIG. 16B is an image of the side illustrating the exemplary working embodiment, and FIG. 16C is an image illustrating the bottom of the exemplary working embodiment. It should be understood that synchronization circuit 110 could also be implemented using an application specific integrated circuit (ASIC).

While synchronization circuit 110 represents one preferred embodiment for implementing synchronization processor 78 (see FIG. 4), as noted above, other circuit designs could be used to implement a circuit-based synchronization processor. It should also be understood that a programmable computing device can instead be used to implement synchronization processor 78. While a computing device-based synchronization processor is likely to be more expensive than a circuit-based synchronization processor, the ubiquitous nature of computing devices suggests that many end-users will already possess a computing device, which when properly programmed, can be used to implement synchronization processor 78.

Figure 9:
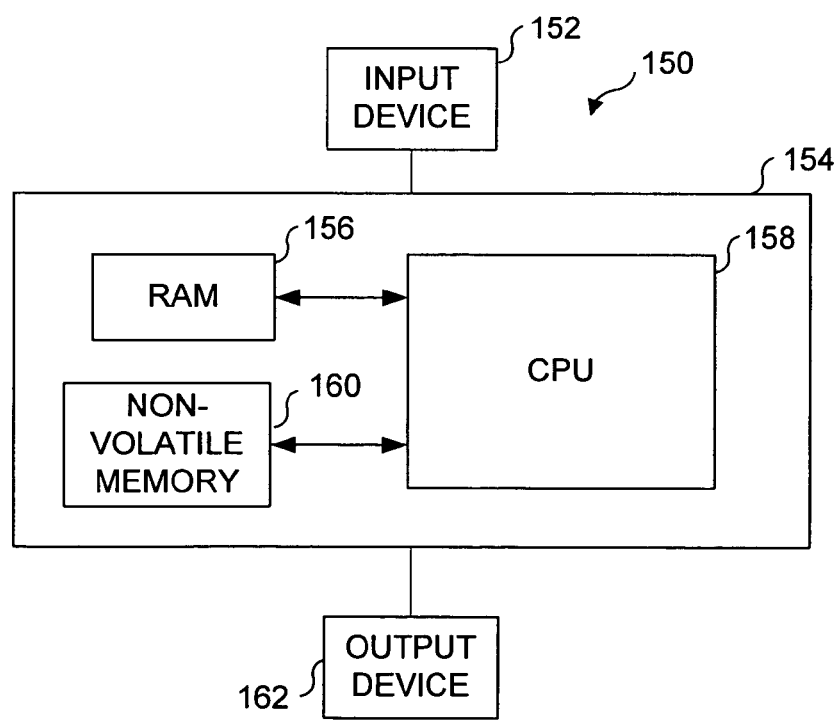

FIG. 9 and the following related discussion are intended to provide a brief, general description of a suitable computing environment for practicing the present invention, where synchronization processor 78 is implemented as a computing device (as opposed to a synchronization circuit). Those skilled in the art will appreciate that the synchronization processor may be implemented by many different types of computing devices, including a laptop and other portable computers, multiprocessor systems, networked computers, mainframe computers, hand-held computers, personal data assistants (PDAs), and on other types of computing devices that include a processor and a memory for storing machine instructions which when implemented by the processor result in the execution of a plurality of functions. In at least one embodiment, those functions are generally consistent with the functions implemented by synchronization circuit 110 of FIG. 6E.

An exemplary computing system 150 suitable for implementing synchronization processor 78 includes a processing unit 154 that is functionally coupled to an input device 152, and an output device 162, e.g., a display. Processing unit 154 includes a central processing unit (CPU 158) that executes machine instructions comprising a signal processing program for implementing the functions of processing scattered imaging ultrasound signals received by a HIFU transducer to achieve a synchronization signal that can be used to enable ultrasound image guided HIFU treatment to be achieved. In at least one embodiment, the machine instructions implement functions generally consistent with those implemented by synchronization circuit 110 (FIG. 6E), although as noted above, it should be understood that the signal processing described in connection with the detailed description of synchronization circuit 110 is intended to be exemplary, rather than limiting of the invention. Those of ordinary skill in the art will recognize that many different signal processing regimes can be employed to process a scattered ultrasound imaging signal received by a HIFU transducer, to provide a synchronization signal. CPUs suitable for this purpose are available, for example, from Intel Corporation, AMD Corporation, Motorola Corporation, and other sources.

Also included in processing unit 154 are a random access memory 156 (RAM) and non-volatile memory 160, which typically includes read only memory (ROM) and some form of memory storage, such as a hard drive, optical drive, etc. These memory devices are bi-directionally coupled to CPU 158. Such storage devices are well known in the art. Machine instructions and data are temporarily loaded into RAM 156 from non-volatile memory 160. Also stored in memory are the operating system software and ancillary software. While not separately shown, it will be understood that a generally conventional power supply will be included to provide the electrical power needed to energize computing system 150.

Input device 152 can be any device or mechanism that facilitates user input into the operating environment, including, but not limited to, a mouse or other pointing device, a keyboard, a microphone, a modem, or other input device. In general, the input device will be used to initially configure computing system 150, to achieve the desired signal processing (i.e., to generate a HIFU synchronization signal based on scattered ultrasound imaging signals received by the HIFU transducer, to enable ultrasound image guided HIFU treatments to be achieved). While not specifically shown in FIG. 9, it should be understood that computing system 150 is logically coupled to HIFU transducer 72 (via diplexer 74), and to power amplifier 76 (see FIG. 4). Configuration of computing system 150 to achieve the desired signal processing includes the steps of loading appropriate signal processing software into non-volatile memory 160, and launching the signal processing application (i.e., loading the signal processing software into RAM 156) so that the signal processing application is ready for use. Output device 162 generally includes any device that produces output information, but will most typically comprise a monitor or computer display designed for human perception of output. It should be recognized that at least one output provided by computing system 150 does not require a display; that output being the synchronization signal (generated by processing the scattered ultrasound imaging signals received by the HIFU transducer and used to control power amplifier 76 of FIG. 4). Accordingly, a conventional computer keyboard and computer display should be considered as exemplary, rather than as limiting on the scope of this embodiment of the present invention.

Figure 10:
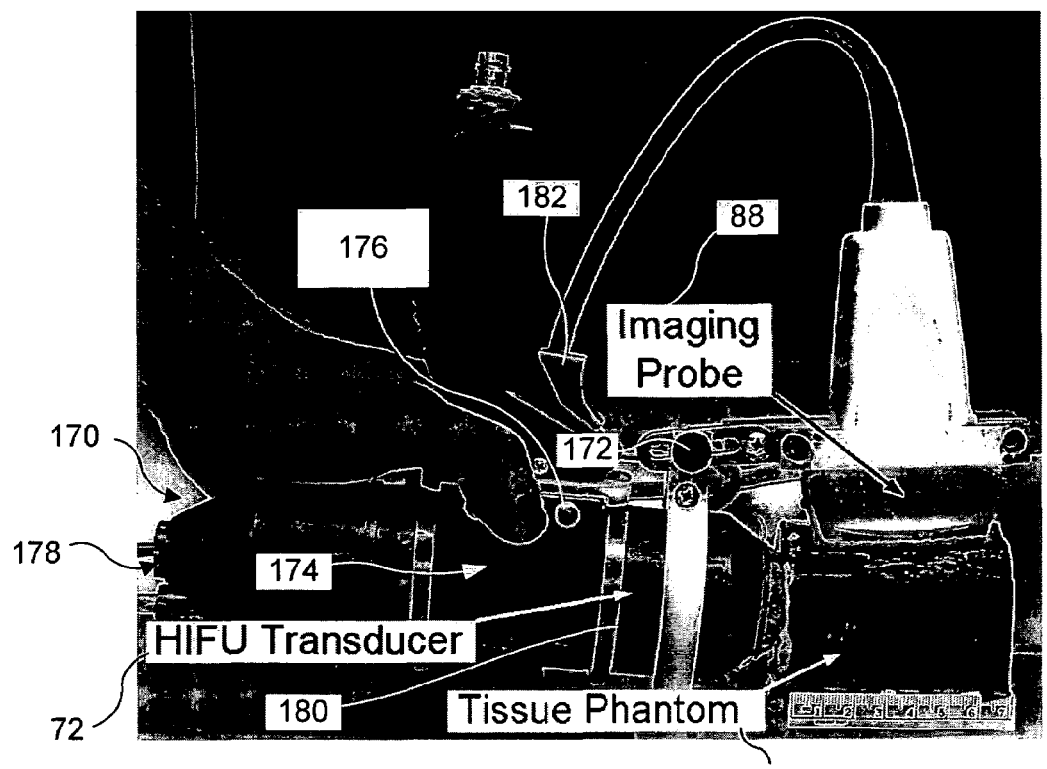
FIGS. 10 and 11 are photographs of a prototype HIFU system tested in conjunction with the exemplary synchronization circuit of FIG. 6E.

As illustrated in FIG. 10, for testing purposes, a custom HIFU transducer housing 170 was built specifically for use with the HIFU system of FIG. 4. A single element transducer was used to implement HIFU transducer 72 in the working prototype of FIG. 10. The single element transducer, disposed in a distal portion 180 of housing 170, is coupled with a stepper motor in a center portion 174. The stepper motor adjusts the depth of the HIFU focus within the scattering target. The single element transducer employed in the working prototype of this embodiment has a diameter of about 33 mm, a radius of curvature of about 55 mm, and a beam width of about 1 mm. The distal portion of the housing is filled with degassed water, although other acoustic coupling materials can alternatively be used, such as a gel. The housing is coupled to a boundary layer (such as a skin layer), and the degassed water filling the distal portion of the housing acoustically couples the HIFU transducer to the housing. The distal end is enclosed by a thin acoustically-transparent plastic membrane. In the working prototype, the plastic membrane was affixed to the distal end (implemented using a plastic cone) of custom HIFU transducer housing 170 with an O-ring, thereby securing the degassed water within the housing. Standard sonography gel can be used to couple the plastic membrane with the boundary layer, although oil, water, or blood could also be used as a coupling medium in clinical practice. The degassed water moves within the distal portion of the housing so that when the stepper motor is used to change the position of the HIFU transducer, sufficient fluid is disposed between the HIFU transducer and the housing to ensure that good acoustic coupling is achieved, without rupturing the thin plastic membrane. Button 176 in center portion 174 enables the user to actuate the stepper motor, and trigger 182 is used to actuate user-controlled switch 80 of FIG. 4, for controlling the HIFU burst. The button configuration was later modified such that a button 182a (see FIG. 11) was used to actuate the user-controlled switch, so that the handle could be removed according to user preferences. Cables that supply power to the HIFU transducer and control the stepper motor are disposed in a proximal portion 178 of housing 170. Axially translating a single-element transducer to achieve a desired focal depth was chosen as an alternative to a phased-array transducer, to reduce overall complexity. However, it should be understood that the present invention can be implemented using a phased array type HIFU transducer. Phased arrays require a separate power amplifier for each array element and control circuitry to adjust focal depth, which increases the overall complexity of this system.

Figure 11:
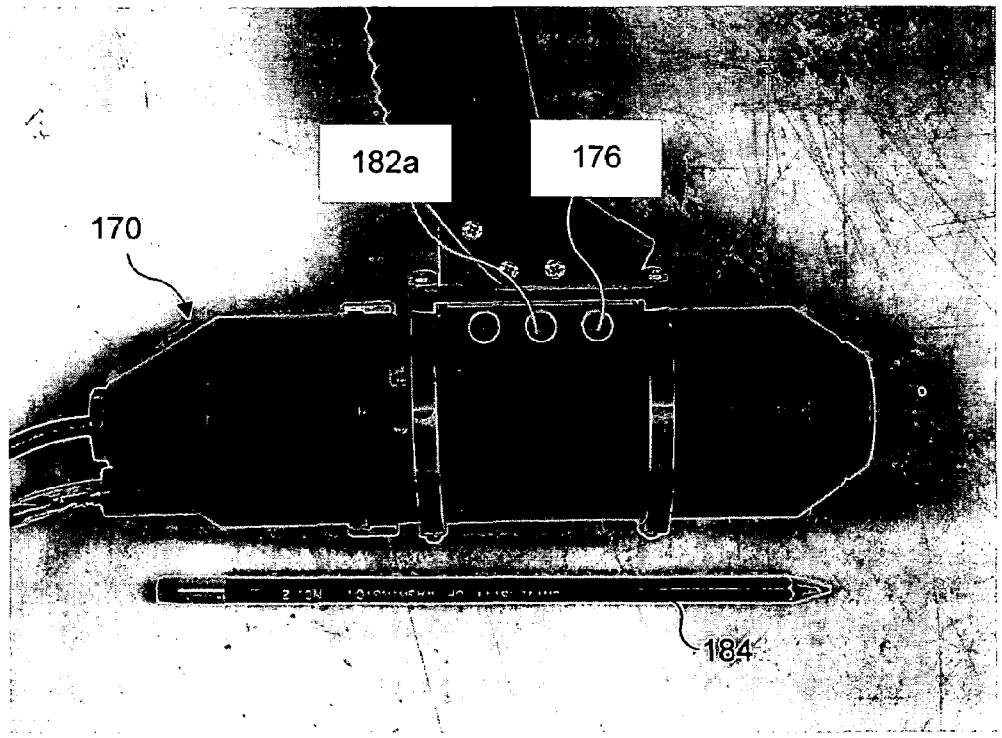

A frame 172 was employed to maintain a desired spatial orientation between the HIFU transducer and the ultrasound imaging probe. The frame incorporates a variety of adjustment structures enabling the frame to accommodate a range of positions, so that once a desirable spatial orientation is achieved, the adjustment structures (e.g., clamps and screws, although other adjustment structures could be used instead, as will be recognized by those of ordinary skill in the art) can be tightened to maintain the desired spatial orientation. The working prototype of this exemplary embodiment was used with a gel tissue phantom 92a as a scattering target. Gel tissue phantoms mimic the acoustic properties of human tissue, and are often used in testing ultrasound equipment. FIG. 11 is a photograph of housing 170 and a standard pencil 184, to provide an indication of the relative size of housing 170. Note that FIGS. 10 and 11 do not show the synchronization circuit, the amplifier, or the ultrasound imaging system.

As indicated in FIG. 4, the HIFU system of this embodiment includes the synchronization processor, the power amplifier, and the HIFU transducer. Such a HIFU system can readily-be made portable (in the sense that such a HIFU system can be made sufficiently small to be easily transported by a single person), if a compact, lightweight amplifier is used. The working prototype of this embodiment used a Class-D amplifier measuring 30×23×16 cm and weighing 5 kg, but this power amplifier could easily be replaced by a smaller and lighter unit. Thus, one aspect of the present invention is directed to a portable HIFU system including a synchronization processor configured to process ultrasound imaging signals received by the HIFU transducer to enable synchronization between the HIFU transducer and a non-specific ultrasound imaging system.

Empirical studies were conducted using the working prototype embodiment of synchronization circuit 110 discussed above and a HIFU system enclosed in housing 170. Synchronized operation was tested by using a charge-coupled device (CCD) camera and two different ultrasound imaging systems, including a SonoSite 180™ and an ATL/Phillips HDI 1000™, to monitor the formation of a lesion in gel tissue phantom 92a (see FIG. 10). When HIFU is applied, bovine serum albumin (BSA) in the gel tissue phantom thermally denatures and becomes opaque, which provides an optical visualization of lesion formation. Plastic microspheres, approximately 10 μm in diameter, were added to the gel tissue phantom to make the scattering characteristics of the gel more like those of human tissue.

The ultrasound imaging system was set to B-mode imaging modality and to an imaging depth of 4.5 cm, which is approximately the depth of the tissue equivalent gel tissue phantom. The phasing and duration of the HIFU gating signal were adjusted prior to the experiment such that the interference was relegated to the edges of the ultrasound image. An inductor-capacitor matching circuit transformed the impedance of the HIFU transducer to 50Ω at its resonant frequency of 3.1 MHz, which is a load that the Class-D amplifier used in the empirical studies can drive at 100 W of electrical power. The time-averaged electrical power used to drive the transducer during the experiment was approximately 40 W, corresponding to a 40% duty cycle for the HIFU burst. Images from the CCD camera and the ultrasound imager were recorded during the experiment, and then post processed into a single video file. The start of the 60 second HIFU exposure was indicated by the appearance of interference in the B-mode recording and indicated by an experimenter queue in the CCD recording. Thus, the two videos could be synchronized in time before they were combined into one file.

Figure 12A:
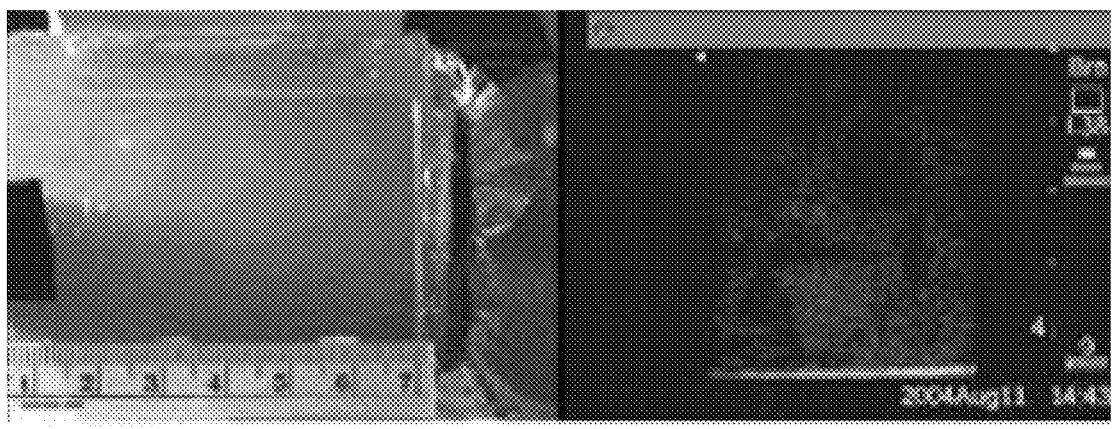
FIGS. 12A-12C are composite images, each respectively including both a photograph of a gel tissue phantom and an ultrasound image, ultrasound each image representing various stages of the application of HIFU waves to the gel tissue phantom.
Figure 12B:
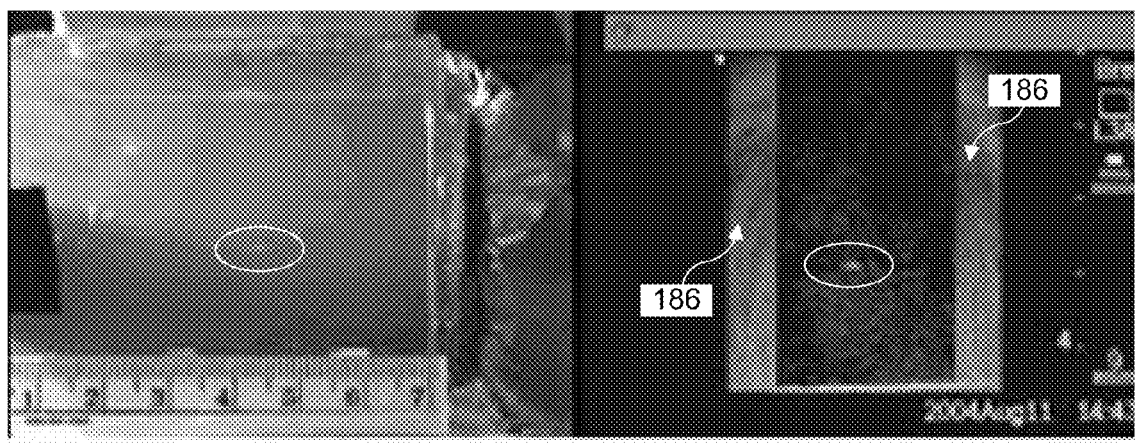
Figure 12C:
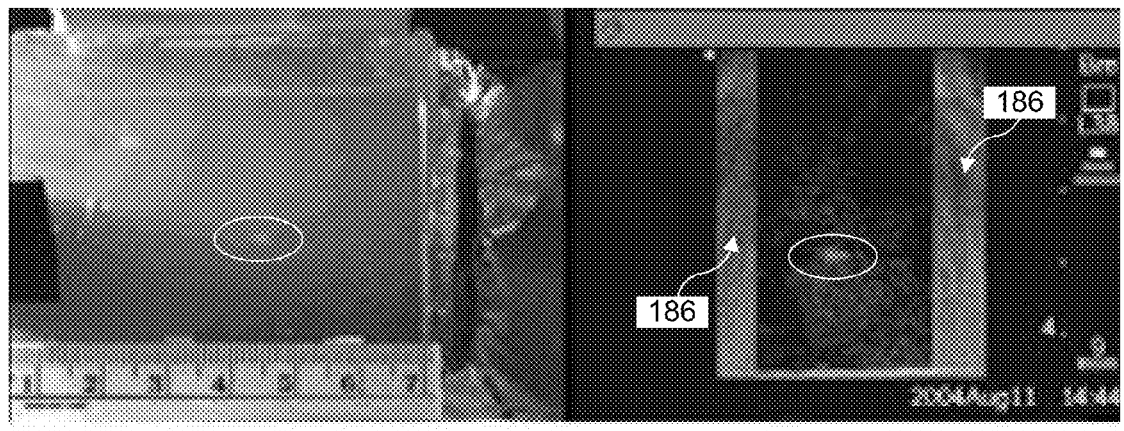

Selected frames of the empirical data are shown in FIGS. 12A-12C to illustrate the performance of the empirical test system. Each image is a composite of both an optical image of the gel tissue phantom (i.e., gel phantom 92a of FIG. 10) and an ultrasound image. CCD-recorded optical images are on the left of each Figure and B-mode ultrasound images are on the right of each Figure. In both the optical images and the B-mode images, the HIFU transducer is on the right and is transmitting to the left, and the imaging probe is on the top and transmitting downwardly. The sequence of the images is as follows. The images in FIG. 12A were collected before HIFU began, the images in FIG. 12B were collected after 16 seconds of HIFU exposure, and the images in FIG. 12C were collected after 34 seconds of HIFU exposure. The lesion and the bright spot are circled in the images of FIG. 12B and FIG. 12C. A bright spot is visible in the center of the B-mode images in FIGS. 12B and 12C. The lesion in the gel tissue phantom is visible as a small, light-colored, cigar-shaped area in the center of the optical images in FIGS. 12B and 12C. By visual inspection, the size, shape, and location of the bright spot correlate well with the size, shape, and location of the lesion in the gel tissue phantom. This result agrees with previous studies that compare the bright spot in an ultrasound image (generally corresponding to the focal region of the HIFU burst) with physical lesions. Referring to the B-mode image portion of FIG. 12B and FIG. 12C (i.e., the images on the right of each Figure), interference 186 caused by the HIFU burst only appears on the sides (or fringes) of the B-mode images. The center portion of each ultrasound image is unaffected and therefore available for target visualization. Enabling a portion of the ultrasound image (preferably a center portion, although if desired noise could be shifted to the center leaving the fringes free of noise) to be free of interference from a HIFU waves during simultaneous ultrasound imaging and HIFU treatment was the intended result of the empirical study. The synchronization technique of this exemplary embodiment performed as intended.

Figure 13A:
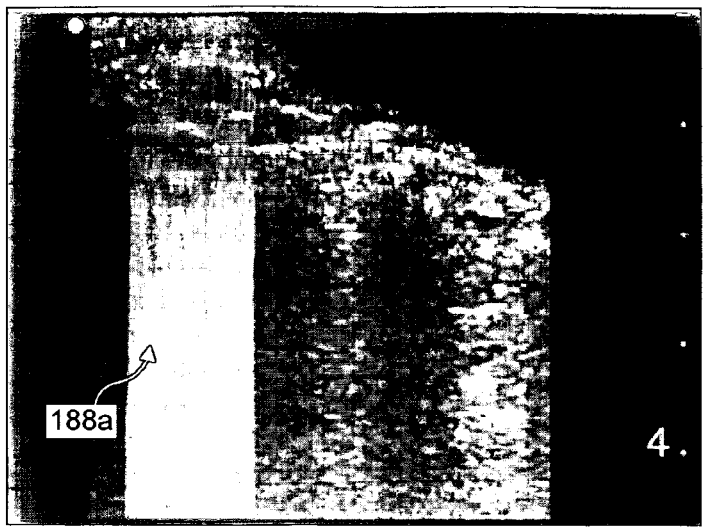
FIGS. 13A-13C are ultrasound images generated using synchronization techniques in accord with one embodiment, wherein noise in each ultrasound image due to simultaneous HIFU application has been shifted to the fringes of the ultrasound image.
Figure 13B:
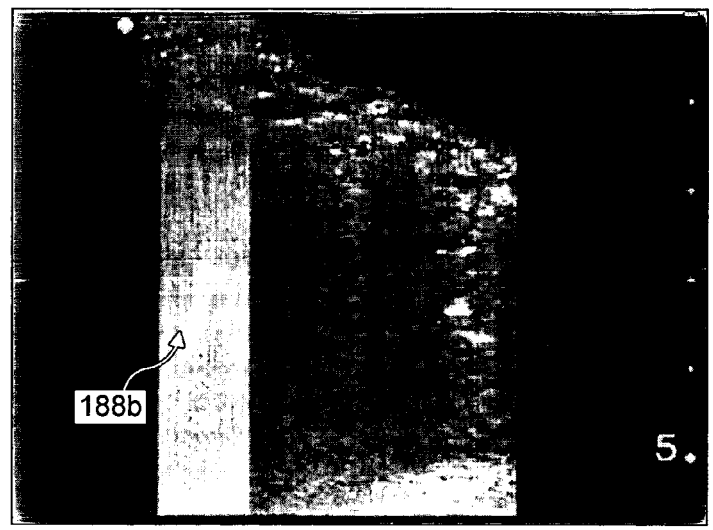
Figure 13C:
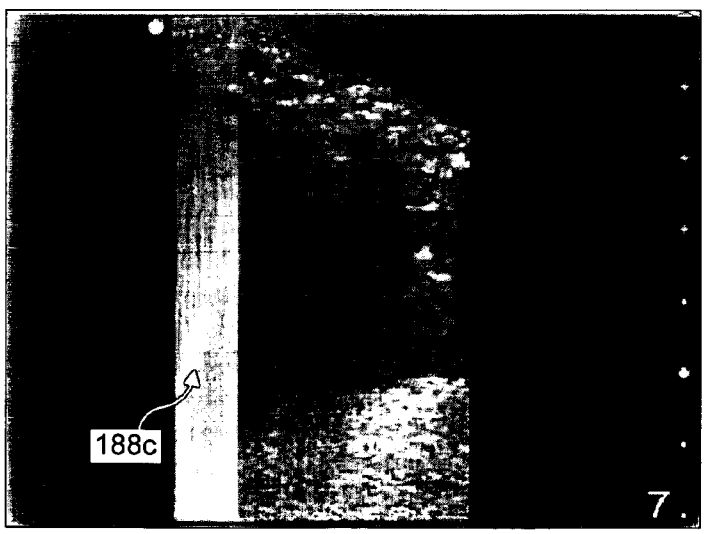

Additional results were obtained from a similar method, where a HIFU transducer and an imaging probe were both submerged in water and a sponge was used to scatter ultrasound. HIFU was synchronized with an imager that was operating in B-mode and then using color Doppler. In both cases, the imaging depth was changed while the HIFU was synchronized and transmitting. The sequence of ultrasound images in FIGS. 13A-13C and 14A-14C demonstrate the ability of HIFU systems including a synchronization circuit in accord with the present invention to adapt in real-time, so as to remain synchronized even when the imaging depth is changed. The ultrasound images of FIGS. 13A-13C represent a sequence of B-mode ultrasound images as the imaging depth changes. In particular, FIG. 13A is a B-mode ultrasound image generated using an imaging depth of 4.5 cm, FIG. 13B is a B-mode ultrasound image generated using an imaging depth of 5.5 cm, and FIG. 13C is a B-mode ultrasound image generated using an imaging depth of 7.0 cm. Note that the total area of interference 188a, 188b, and 188c is different in each ultrasound image. As noted above, the length of the gating pulse relative to the period of the frame rate determines the total area of interference on the ultrasound image. The area of interference will increase as the burst length increases, or as the frame period decreases (i.e., as the rate increases). In this case, increasing the depth of the image means more time is required to generate each frame. Because the HIFU is on for the same amount of time at each depth, at greater depths, the HIFU interference covers proportionately less of the image. The operator is not required to manually control the duration of the HIFU bursts to ensure that the interference is limited to the fringes of the ultrasound image, since the synchronization circuit automatically provides that function.

Figure 14A:
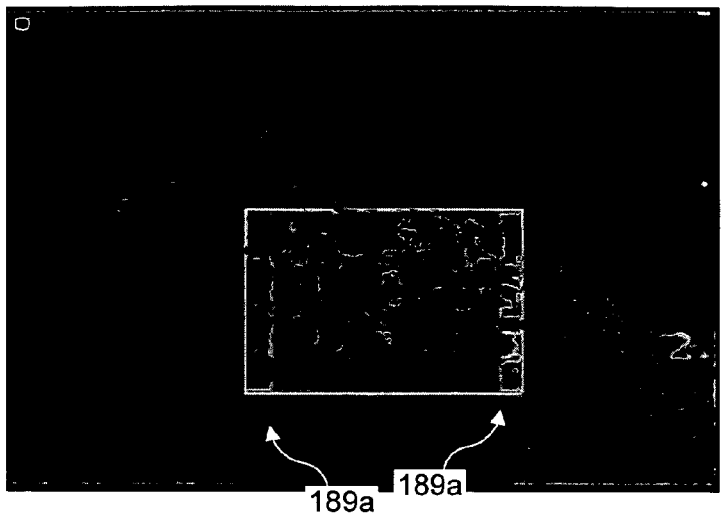
FIGS. 14A-14C are ultrasound images generated using synchronization techniques provided by one exemplary embodiment, wherein noise in each ultrasound image due to simultaneous HIFU application has been shifted to the fringes of the ultrasound image.
Figure 14B:
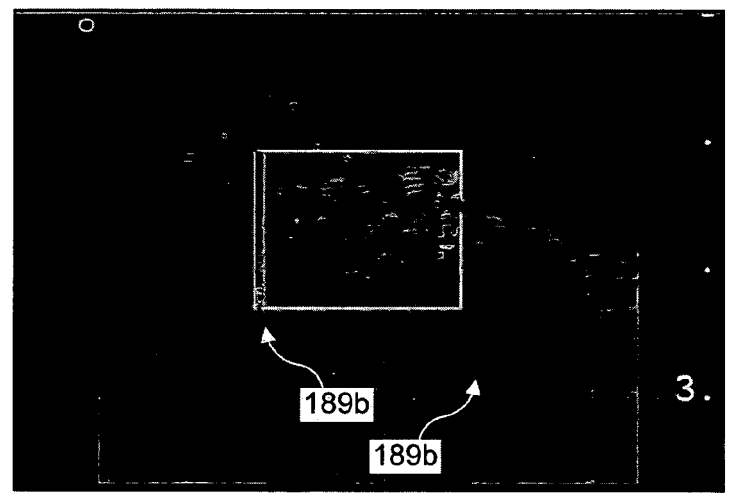
Figure 14C:
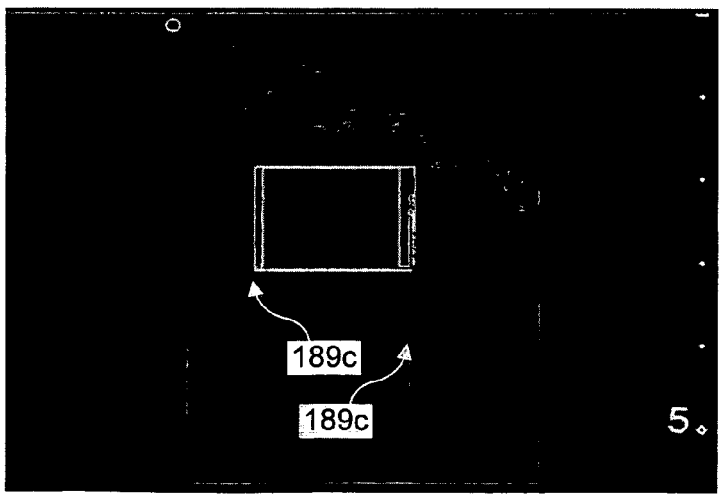

FIG. 14A is a Color Power Doppler ultrasound image generated using an imaging depth of 2.5 cm, FIG. 14B is a Color Power Doppler ultrasound image generated using an imaging depth of 3.5 cm, and FIG. 14C is a Color Power Doppler ultrasound image generated using an imaging depth of 5.5 cm. Again, note that the total area of interference 189a, 189b, and 189c is different in each ultrasound image.

In a particularly preferred embodiment, the HIFU transducer is used as a receiver to detect scattered ultrasound imaging waves. The scattered ultrasound imaging waves are manipulated by a synchronization processor to achieve a synchronization signal used to synchronize HIFU bursts with ultrasound imaging waves, so that acoustic interference produced in ultrasound image is stabilized and confined to the edges of the image. While the use of the HIFU transducer as a receiver is considered to be a particularly elegant solution, it should be understood that a dedicated receiver could instead be incorporated into either in ultrasound, imaging probe or a HIFU therapy probe, or a stand-alone dedicated receiver could instead be used, so that the dedicated receiver could detect scattered ultrasound imaging waves for processing by the synchronization circuit.

Figure 15:
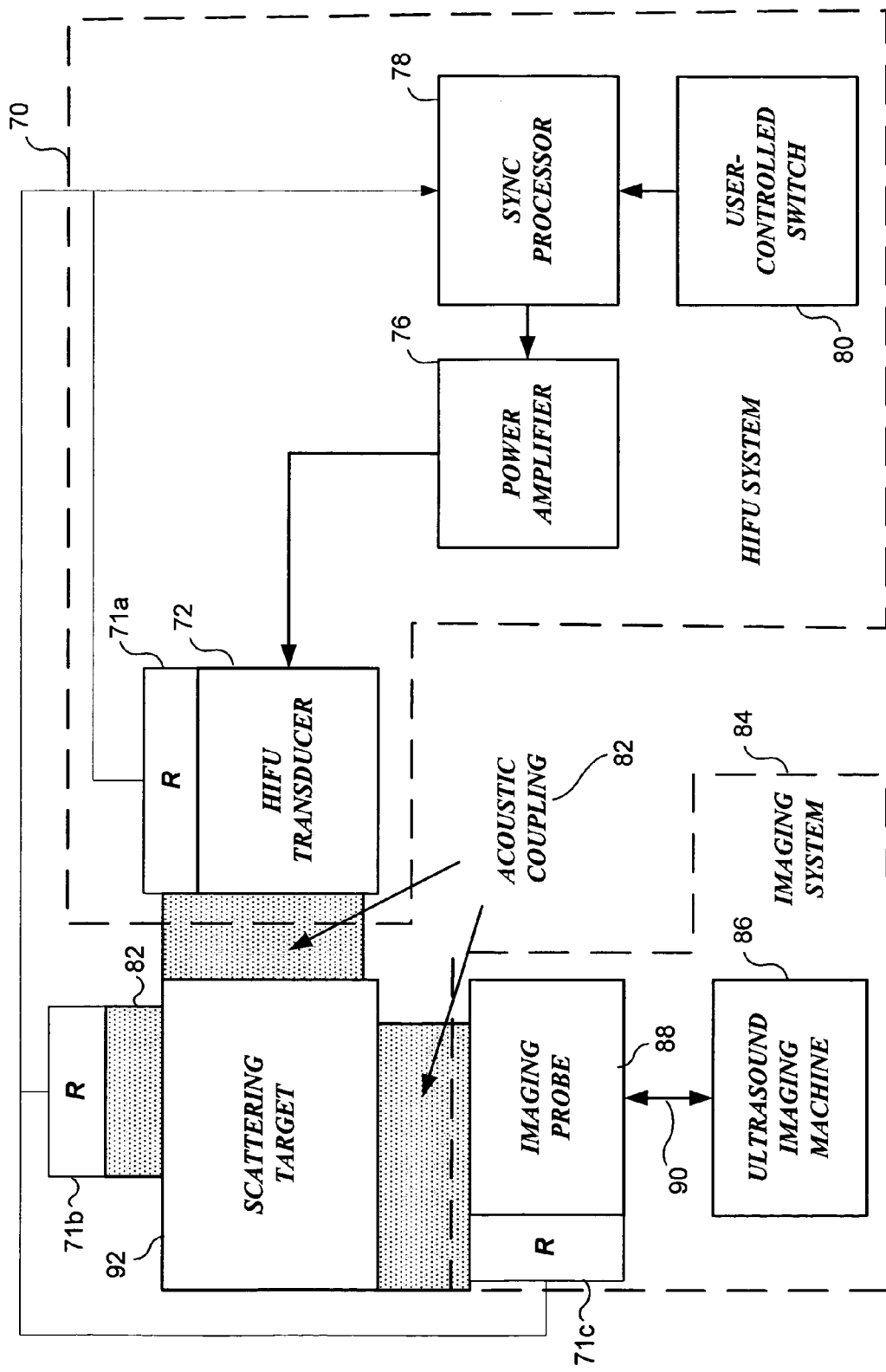
FIG. 15 is a block diagram illustrating an embodiment in which a dedicated receiver is employed to detect scattered ultrasound imaging waves, producing a signal for processing by a synchronization processor to enable a HIFU transducer to be synchronized with an ultrasound imaging transducer.

FIG. 15 is a high-level functional block diagram of another embodiment for implementing the present invention, in which a dedicated receiver is used to collect the scattered ultrasound imaging signals in place of using the HIFU transducer for that purpose. It should be understood that FIG. 15 is based on FIG. 4, and includes many of the same elements. Where the same elements in the two circuits serve an identical purpose, there is no need to discuss those elements in further detail. Instead, the following description of FIG. 15 will focus on the differences between the block diagrams of FIG. 4 (using the HIFU transducer is a receiver to collect scattered ultrasound imaging signals for processing by the synchronization processor) and FIG. 15 (using a dedicated receiver to collect scattered ultrasound imaging signals for processing by the synchronization processor). FIG. 15 includes dedicated receivers 71a, 71b, and 71c. It should be understood that while a plurality of dedicated receivers could be implemented, only a single receiver is required. Each receiver employed is logically coupled to synchronization processor 78, and there is no longer any need for diplexer 74. Receiver 71a is disposed adjacent to HIFU transducer 72. Such a configuration can be achieved by incorporating receiver 71a into a HIFU therapy probe (such as the HIFU therapy probe defined by housing 170, in FIGS. 10 and 11).

Receiver 71b is a stand-alone receiver (i.e., a receiver that is not incorporated into either a HIFU therapy probe or in ultrasound imaging probe). The position of receiver 71b is selected to ensure that the receiver can receive scattered ultrasound imaging signals from the ultrasound imaging probe. In some implementations, it will be desirable to secure receiver 71b to frame 172 (see FIG. 10), to maintain a desired spatial orientation between the ultrasound imaging probe, the HIFU therapy probe, and the receiver. Receiver 71c is disposed adjacent to ultrasound imaging probe 88. Such a configuration can be achieved by incorporating receiver 71b into the ultrasound imaging probe (which would require a manufacturer of ultrasound imaging equipment to recognize the need for such an additional receiver to be incorporated into an ultrasound imaging probe, or the modification of an existing ultrasound imaging probe), or simply by attaching a separate receiver to an existing ultrasound imaging probe. Regardless of how the receiver is implemented (i.e., one of receivers 71a-71c, or some combination thereof), the scattered ultrasound imaging waves collected by the receiver(s) are manipulated by the synchronization processor to achieve a synchronization signal as described above.

Empirical testing can be performed to determine if a plurality of such receivers provide an advantage over a single receiver. Such testing can also be used to determine if it would be beneficial to average the signals collected by a plurality of receivers, and then provide the averaged signal to the synchronization processor for further manipulation. The receivers can be implemented using any conventional receiver device that is capable of collecting scattered ultrasound imaging waves, as described above. Preferably, any receiver will be acoustically coupled to the scattering target using an acoustic coupling media, generally as described above, although such a preference is not intended to represent a limitation on the invention.

It should be understood that yet another aspect of the present invention is directed to a receiver and synchronization processor, which are configured to be used with a HIFU therapy probe and an ultrasound imaging probe. The receiver and synchronization processor enable the activation of the HIFU therapy probe to be synchronized to the ultrasound imaging probe, such that at least part of an ultrasound image generated using data collected by the ultrasound imaging probe does not include interference due to HIFU waves generated by the HIFU therapy probe. The receiver can comprise any suitable receiver device that is capable of collecting scattered ultrasound imaging waves, as described above. The synchronization processor can be implemented using a programmable computing device, an application specific integrated circuit (ASIC), or a synchronization circuit, each of which have been discussed above. The receiver can be positioned independently of the ultrasound imaging probe and the HIFU therapy probe, as illustrated in FIG. 15, or the receiver can be incorporated into or coupled with either the ultrasound imaging probe or the HIFU therapy probe (also as illustrated in FIG. 15). The receiver is logically coupled to the synchronization processor. The synchronization processor will be logically coupled to a power amplifier that is used to energize the HIFU transducer in the HIFU therapy probe. As discussed above, in a particularly preferred embodiment, the synchronization processor is also logically coupled to a user-activated switch for selectively controlling the HIFU therapy probe, although such a configuration should not be considered to limit the invention. Thus, while a particularly preferred embodiment of the present invention comprises a HIFU therapy probe that includes the synchronization processor in the HIFU therapy probe, it should be understood that other preferred embodiments of the present invention are directed to a receiver and synchronization processor for use with existing HIFU therapy probes and ultrasound imaging probes.

ADVANTAGES OF THE INVENTION

No modification of a clinical imager is required, and as a result, the imager company has no added liability when used with therapy.

Any imager, any modality, and any user adjustment can be used, while still retaining synchronization between the imaging and therapy ultrasound sources. Thus, the best imager for the application can be used.

There is no added complexity for the user. The synchronization between the imaging and therapy ultrasound sources is inherent in the system.

The synchronization adapts to user-adjustable controls associated with the imaging system (e.g., switching imaging modalities, or imaging depth).

The synchronization works with different imaging modalities (e.g., Doppler imaging and B-mode imaging).

The expense of the required components are minimal, and in fact, the added receiver electronics provide enhanced capability.

While the preferred embodiments discussed above have been described in terms of synchronizing therapeutic HIFU with ultrasound imaging, it should be understood that the present invention encompasses synchronizing any type of ultrasound with ultrasound used for imaging, such that ultrasound imaging can be combined with ultrasound employed, for some other purpose, without the ultrasound used for non-imaging purposes interfering with the ultrasound imaging. For example, ultrasound can be used to provide physical therapy (generally by warming tissue). The levels of ultrasound used for such physical therapy generally are not sufficiently energetic to be described as HIFU. The synchronization techniques and apparatus of the present invention can be used to synchronize ultrasound used to provide physical therapy with ultrasound used for imaging. Ultrasound has also been investigated for use in conjunction with drug delivery. Again, the synchronization techniques and apparatus of the present invention can be used to synchronize ultrasound used in conjunction with drug delivery with ultrasound used for imaging, such that the ultrasound used in conjunction with drug delivery does not interfere with the ultrasound used for imaging. Some applications of ultrasound involve using ultrasound to excite micro-bubble based contrast agents, while simultaneously using ultrasound imaging to observe the contrast agent's perfusion into a target region. Again, the synchronization techniques of the present invention can be used to prevent ultrasound used to excite or activate such contrast agents (or other agents) from interfering with ultrasound used to generate an image. Thus, it should be understood that the synchronization techniques and apparatus of the present invention are not limited to preventing HIFU from interfering with ultrasound imaging, as the same techniques can be used to prevent other types of ultrasound from interfering with ultrasound used for imaging purposes.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for synchronizing non-imaging ultrasound waves and ultrasound imaging waves produced by an ultrasound imaging system, so at least a portion of an ultrasound image produced by the ultrasound imaging system is free from interference due to the non-imaging ultrasound waves, comprising the steps of:
   (a) producing an output signal in response to receiving scattered ultrasound imaging waves independently of the ultrasound imaging system;
   (b) manipulating the output signal to generate a synchronization signal; and
   (c) using the synchronization signal to selectively control generation of the non-imaging ultrasound waves, such that at least a portion of the ultrasound image is free from interference due to the non-imaging ultrasound waves;
   wherein the step of producing the output signal comprises the step of using a receiver to detect the scattered ultrasound imaging waves, the receiver being independent of an ultrasound imaging probe that generates the ultrasound imaging waves and of a transducer generating the non-imaging ultrasound waves.

2. The method of claim 1, wherein the non-imaging ultrasound waves comprise high intensity focused ultrasound (HIFU) waves.

3. The method of claim 1, wherein the step of producing the output signal comprises the step of using at least one of a receiver disposed proximate to an ultrasound imaging transducer of the ultrasound imaging system, and a receiver disposed proximate to a transducer generating the non-imaging ultrasound waves.

4. The method of claim 1, wherein the step of manipulating the output signal to generate the synchronization signal comprises the step of using a computing device to generate the synchronization signal.

5. The method of claim 1, wherein the step of manipulating the output signal to generate the synchronization signal comprises the step of using a synchronization circuit to generate the synchronization signal.

6. The method of claim 1, wherein the step of manipulating the output signal to generate the synchronization signal comprises the step of automatically generating the synchronization signal using at least one of a computing device and a synchronization circuit.

7. The method of claim 1, wherein the step of manipulating the output signal to generate the synchronization signal comprises the steps of:
   (a) detecting the output signal;
   (b) determining an envelope of the output signal; and
   (c) generating a pulse for triggering a transducer that generates the non-imaging ultrasound waves.

8. The method of claim 1, wherein the step of manipulating the output signal to generate the synchronization signal comprises the steps of:
   (a) amplifying the output signal;
   (b) averaging a plurality of amplitudes defining the output signal to generate an averaged output signal;
   (c) amplifying the averaged output signal;
   (d) clamping the averaged output signal to insure that the averaged output signal does not exceed a maximum value, thereby generating a clamped signal;
   (e) using the clamped signal to generate a pulsed signal for triggering a transducer that generates the non-imaging ultrasound waves; and
   (f) combining the pulsed signal for triggering a transducer that generates the non-imaging ultrasound waves with a signal from a user control switch to generate the synchronization signal, such that the synchronization signal is used to selectively control the transducer that generates the non-imaging ultrasound waves only when a user has activated the user control switch.

9. The method of claim 1, wherein the step of manipulating the output signal to generate the synchronization signal comprises the step of eliminating false triggers.

10. The method of claim 2, wherein the step of producing the output signal comprises the step of using a HIFU transducer configured to generate the HIFU waves as a receiver to detect the scattered ultrasound imaging waves.

11. The method of claim 7, wherein the step of manipulating the output signal to generate the synchronization signal further comprises the step of combining the pulse for triggering the transducer that generates the non-imaging ultrasound waves with a signal from a user control switch to generate the synchronization signal, such that the synchronization signal is used to selectively control the transducer that generates the non-imaging ultrasound waves only when a user has activated the user control switch, regardless of the existence of a pulse that has been generated based on the output signal.

12. A method for synchronizing non-imaging ultrasound waves and ultrasound imaging waves, so that interference in an ultrasound image due to the non-imaging ultrasound waves is limited to only a portion of the ultrasound image, comprising the steps of:
   (a) using a transducer that generates non-imaging ultrasound waves to detect scattered ultrasound imaging waves, the transducer that generates non-imaging ultrasound waves producing an output signal that is indicative of the ultrasound imaging waves that are detected;
   (b) manipulating the output signal to generate a synchronization signal; and
   (c) using the synchronization signal to selectively control generation of the non-imaging ultrasound waves by the transducer that generates non-imaging ultrasound waves, such that interference in the ultrasound image generated using the ultrasound imaging waves due to the non-imaging ultrasound waves is limited to only a portion of the ultrasound image.

13. The method of claim 12, wherein the step of manipulating the output signal to generate the synchronization signal comprises the step of automatically generating the synchronization signal using at least one of a computing device and a synchronization circuit.

14. The method of claim 12, wherein the step of manipulating the output signal to generate the synchronization signal comprises the steps of:
   (a) amplifying the output signal;
   (b) averaging a plurality of amplitudes defining the output signal to generate an averaged output signal;
   (c) amplifying the averaged output signal;
   (d) clamping the averaged output signal to insure that the averaged output signal does not exceed a maximum value, thereby generating a clamped signal; and
   (e) using the clamped signal to generate a pulsed signal for triggering the transducer that generates the non-imaging ultrasound waves.

15. The method of claim 12, wherein the non-imaging ultrasound waves comprise at least one of therapeutic ultrasound waves and high intensity focused ultrasound waves.

16. A method for using ultrasound to simultaneously image a target area and apply therapeutic ultrasound waves to a treatment site disposed within said target area, comprising the steps of:
   (a) using an ultrasound imaging system to generate an ultrasound image of the target area;
   (b) without using the ultrasound imaging system, detecting the scattered ultrasound imaging waves generated by the ultrasound imaging system, producing an output signal that is indicative of the ultrasound imaging waves;
   (c) manipulating the output signal to generate a synchronization signal; and
   (d) using the synchronization signal to selectively control a transducer that generates the therapeutic ultrasound waves, such that:
      (i) the synchronization signal ensures that at least a portion of the ultrasound image is free from interference due to the therapeutic ultrasound waves; and
      (ii) a focal point of the therapeutic ultrasound transducer is able to be visualized in the ultrasound image generated by the ultrasound imaging system without being obscured by interference caused by the therapeutic ultrasound waves as they induce a therapeutic effect at the treatment site.

17. The method of claim 16, wherein the step of detecting the scattered ultrasound imaging waves comprises the step of using the therapeutic ultrasound transducer as a receiver to detect the scattered ultrasound imaging waves.

18. The method of claim 16, wherein the therapeutic ultrasound waves comprise high intensity focused ultrasound waves.

19. A system for enabling non-imaging ultrasound to be applied to a target area while simultaneously imaging the target area with an ultrasound imaging system, to enable real-time ultrasound imaging of the target area to be achieved while applying non-imaging ultrasound to the target area, comprising:
   (a) a receiver configured to detect scattered ultrasound imaging waves generated by an ultrasound imaging transducer included within the ultrasound imaging system, independently of the ultrasound imaging system, producing an output signal that is indicative of the ultrasound imaging waves; and (b) a synchronization processor logically coupled to the receiver, the synchronization processor being configured to generate a synchronization signal to be used to control a transducer employed for producing non-imaging ultrasound waves, so that at least a portion of an ultrasound image generated using the ultrasound imaging transducer does not include interference due to the non-imaging ultrasound waves;

wherein the receiver comprises the transducer that generates the non-imaging ultrasound waves.

20. The system of claim 19, wherein the transducer that generates the non-imaging ultrasound waves comprises a transducer configured to generate high intensity focused ultrasound waves.

21. The system of claim 19, wherein the receiver is configured to be coupled with at least one of an ultrasound imaging probe of the ultrasound imaging system, and a probe that includes the transducer that generates the non-imaging ultrasound waves.

22. The system of claim 19, wherein the synchronization processor is configured to implement the following functions:
(a) detecting the output signal;
(b) determining an envelope of the output signal; and
(c) generating a pulse for triggering the transducer that generates the non-imaging ultrasound waves.

23. The system of claim 19, further comprising a user control switch, wherein the synchronization processor is configured to implement the following functions:
(a) amplifying the output signal;
(b) averaging a plurality of amplitudes defining the output signal to generate an averaged output signal;
(c) amplifying the averaged output signal, to produce an amplified average output signal;
(d) clamping the amplified averaged output signal to insure that the amplified averaged output signal does not exceed a maximum value, thereby generating a clamped signal;
(e) using the clamped signal to generate a pulsed signal for triggering the transducer that generates the non-imaging ultrasound waves; and
(f) combining the pulsed signal for triggering the transducer that generates the non-imaging ultrasound waves with a signal indicative of an active state of the user control switch, to generate the synchronization signal, such that the synchronization signal is used to selectively control the transducer that generates the non-imaging ultrasound waves only when a user has activated the user control switch.

24. The system of claim 19, wherein the synchronization processor comprises at least one of a programmable computing device, an application specific integrated circuit, and a hardware-based synchronization circuit.

25. The system of claim 19, wherein the synchronization processor comprises a hardware-based synchronization circuit that includes:
(a) an amplifier for amplifying the output signal, producing an amplified output signal;
(b) an envelope detector for averaging a plurality of amplitudes of the amplified output signal, to generate an averaged output signal;
(c) an amplifier for amplifying the averaged output signal;

(d) a clamp for clamping the averaged output signal to insure that the averaged output signal does not exceed a maximum value, thereby generating a clamped signal; and
(e) a pulse generator for using the clamped signal to generate a pulsed signal for triggering the transducer that generates the non-imaging ultrasound waves.

26. A synchronization processor configured to enable non-imaging ultrasound waves to be applied to a target area while imaging the target area with an ultrasound imaging system, and to prevent a real-time ultrasound image of the target area from being obscured due to interference caused by the non-imaging ultrasound waves, comprising:
(a) an input configured to be coupled to an output signal from a receiver that is independent of the ultrasound imaging system, but which is configured to detect scattered ultrasound imaging waves generated by an ultrasound imaging transducer that is included within the ultrasound imaging system, the receiver producing the output signal, which is indicative of the ultrasound imaging waves; and
(b) an output configured to be coupled to control activation of a non-imaging transducer, so that the non-imaging transducer is synchronized to produce non-imaging ultrasound waves in regard to production of the ultrasound imaging waves by the ultrasound imaging transducer, so that at least a portion of an ultrasound image generated using the ultrasound imaging transducer does not include interference due to the non-imaging ultrasound waves produced by the non-imaging transducer; and wherein the synchronization processor is configured to implement the following functions:
(a) amplifying the output signal, producing an amplified output signal;
(b) averaging a plurality of amplitudes of the amplified output signal to generate an averaged output signal;
(c) amplifying the averaged output signal to produce an amplified averaged output signal;
(d) clamping the amplified averaged output signal to insure that the amplified averaged output signal does not exceed a maximum value, thereby generating a clamped signal; and
(e) using the clamped signal to generate a pulsed signal at the output of the synchronization processor, for triggering the con imaging transducer to produce non-imaging ultrasound waves.

27. The synchronization processor of claim 26, wherein the synchronization processor comprises at least one of a programmable computing device, an application-specific integrated circuit, and a hardware-based synchronization circuit.

28. The synchronization processor of claim 26, wherein the synchronization processor is further configured to implement the function of combining the pulsed signal for triggering the con imaging transducer with a signal from a user control switch to generate the synchronization signal, such that the synchronization signal is used to selectively control the non-imaging transducer only when a user has activated the user control switch.

29. A therapeutic ultrasound system configured for automatic synchronization with an ultrasound imaging system, to enable real-time ultrasound imaging of a target area to be achieved while applying therapeutic ultrasound to the target area, comprising:
(a) a therapeutic transducer configured to produce therapeutic ultrasound waves;
(b) a receiver configured to detect scattered ultrasound imaging waves generated by an ultrasound imaging transducer included within the ultrasound imaging system, the receiver producing an output signal that is indicative of the ultrasound imaging waves independently of the ultrasound imaging system; and (c) a synchronization processor logically coupled to the receiver, the synchronization processor being configured to generate a synchronization signal used to control activation of the therapeutic transducer in response to the output signal, so that the therapeutic transducer is synchronized in producing the therapeutic ultrasound waves in regard to activation of the ultrasound imaging transducer, and so that at least a portion of an ultrasound image generated with the ultrasound imaging transducer does not include interference due to therapeutic ultrasound waves produced by the therapeutic transducer.

30. The therapeutic ultrasound system of claim 29, wherein the therapeutic transducer is configured to produce high-intensity focused ultrasound waves.

31. A method for synchronizing non-imaging ultrasound waves and ultrasound imaging waves produced by an ultrasound imaging system, so at least a portion of an ultrasound image produced by the ultrasound imaging system is free from interference due to the non-imaging ultrasound waves, comprising the steps of:

(a) providing an ultrasound imaging system including an ultrasound imaging transducer;

(b) providing an ultrasound receiver that is not part of the ultrasound imaging system;

(c) using the ultrasound receiver for receiving scattered ultrasound imaging waves that were produced by the ultrasound imaging transducer, producing an output signal in response thereto;

(d) manipulating the output signal to generate a synchronization signal; and (e) using the synchronization signal to selectively control generation of the non-imaging ultrasound waves, such that at least a portion of the ultrasound image is free from interference due to the non-imaging ultrasound waves.

32. A therapeutic ultrasound system configured for automatic synchronization with an ultrasound imaging system that includes an ultrasound imaging transducer for producing ultrasound imaging waves, to enable real-time ultrasound imaging of a target area to be achieved while applying therapeutic ultrasound to the target area, comprising:

(a) a therapeutic transducer configured to produce therapeutic ultrasound waves;

(b) a receiver configured to detect scattered ultrasound imaging waves generated by the ultrasound imaging transducer included within the ultrasound imaging system, the receiver producing an output signal that is indicative of the ultrasound imaging waves detected, where the receiver is not part of the ultrasound imaging system; and (c) a synchronization processor logically coupled to receive the output signal from receiver, the synchronization processor being configured to generate a synchronization signal used to control activation of the therapeutic transducer in response to the output signal, so that the therapeutic transducer is synchronized in producing the therapeutic ultrasound waves in regard to activation of the ultrasound imaging transducer, and so that at least a portion of an ultrasound image generated with the ultrasound imaging transducer does not include interference due to therapeutic ultrasound waves produced by the therapeutic transducer.

* * * * *